(12) United States Patent
Elmaleh

(10) Patent No.: US 10,525,005 B2
(45) Date of Patent: *Jan. 7, 2020

(54) CROMOLYN COMPOSITIONS AND METHODS THEREOF

(71) Applicant: The General Hospital Corporation, Boston, MA (US)

(72) Inventor: David R. Elmaleh, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,980

(22) Filed: Dec. 4, 2017

(65) Prior Publication Data

US 2018/0153803 A1 Jun. 7, 2018

Related U.S. Application Data

(63) Continuation-in-part of application No. 14/893,487, filed as application No. PCT/US2014/039118 on May 22, 2014, now Pat. No. 9,861,608.

(60) Provisional application No. 61/826,798, filed on May 23, 2013.

(51) Int. Cl.
| | |
|---|---|
| *A61K 9/00* | (2006.01) |
| *A61K 9/14* | (2006.01) |
| *A61K 31/352* | (2006.01) |
| *A61M 16/14* | (2006.01) |
| *A61M 15/00* | (2006.01) |
| *A61P 11/06* | (2006.01) |

(52) U.S. Cl.
CPC .............. *A61K 9/0075* (2013.01); *A61K 9/14* (2013.01); *A61K 31/352* (2013.01); *A61M 15/0085* (2013.01); *A61M 16/14* (2013.01); *A61P 11/06* (2018.01); *A61M 2202/064* (2013.01)

(58) Field of Classification Search
CPC ...... A61K 9/0075; A61K 31/352; A61K 9/14; A61P 11/06; A61M 16/14; A61M 15/0085; A61M 2202/064
See application file for complete search history.

(56) References Cited

U.S. PATENT DOCUMENTS

| | | | |
|---|---|---|---|
| 3,419,578 A | 12/1968 | Fitzmaurice et al. |
| 3,634,582 A | 1/1972 | Hartley et al. |
| 3,686,412 A | 8/1972 | Fitzmaurice et al. |
| 3,957,965 A | 5/1976 | Hartley et al. |
| 4,120,285 A | 10/1978 | Nugent |
| 4,405,735 A | 9/1983 | Wiezer et al. |
| 4,429,545 A | 2/1984 | Steinberg |
| 4,481,206 A | 11/1984 | Spiegel et al. |
| 4,996,296 A | 2/1991 | Pecht et al. |
| 5,376,386 A | 12/1994 | Ganderton et al. |
| 5,567,720 A | 10/1996 | Averback |
| 5,594,142 A | 1/1997 | Gaa et al. |
| 5,655,523 A | 8/1997 | Hodson et al. |
| 5,830,920 A | 11/1998 | Chucholowski et al. |
| 5,904,937 A | 5/1999 | Augello et al. |
| 6,168,776 B1 | 1/2001 | Klunk et al. |
| 6,197,963 B1 | 3/2001 | Hirschmann et al. |
| 6,309,623 B1 * | 10/2001 | Weers .................. A61K 9/0073 424/45 |
| 6,696,039 B2 | 2/2004 | Kung et al. |
| 6,911,466 B2 | 6/2005 | Koo et al. |
| 6,946,116 B2 | 9/2005 | Kung et al. |
| 6,972,127 B2 | 12/2005 | Schenk |
| 7,160,559 B1 | 1/2007 | McGee et al. |
| 7,858,803 B2 | 12/2010 | Elmaleh et al. |
| 8,381,454 B1 | 2/2013 | Robinson |
| 8,613,920 B2 | 12/2013 | Lieberburg et al. |
| 8,617,517 B2 | 12/2013 | Elmaleh et al. |
| 8,765,742 B2 | 7/2014 | Hilfiker et al. |
| 9,283,230 B2 | 3/2016 | Clunas et al. |
| 9,855,276 B2 | 1/2018 | Elmaleh |
| 9,861,608 B2 | 1/2018 | Elmaleh et al. |
| 9,913,847 B2 | 3/2018 | Elmaleh |
| 9,918,992 B2 | 3/2018 | Elmaleh |
| 9,925,282 B2 | 3/2018 | Elmaleh et al. |
| 9,968,618 B1 | 5/2018 | Elmaleh |
| 1,005,853 A1 | 8/2018 | Elmaleh |
| 1,018,875 A1 | 1/2019 | Elmaleh |
| 10,245,331 B2 | 4/2019 | Elmaleh |
| 10,251,961 B2 | 4/2019 | Elmaleh |
| 10,398,704 B2 | 9/2019 | Elmaleh |
| 10,406,164 B2 | 9/2019 | Elmaleh |
| 10,413,551 B2 | 9/2019 | Elmaleh |
| 2002/0009491 A1 | 1/2002 | Rothbard et al. |
| 2002/0016359 A1 | 2/2002 | Hellberg et al. |
| 2002/0091100 A1 | 7/2002 | Lezdey et al. |
| 2002/0107173 A1 | 8/2002 | Friedhoff et al. |
| 2004/0176469 A1 | 9/2004 | Thomas |
| 2004/0223918 A1 | 11/2004 | Pham et al. |
| 2004/0259952 A1 | 12/2004 | Abbas et al. |
| 2006/0051319 A1 | 3/2006 | Yoo |
| 2006/0159629 A1 | 7/2006 | Tarara et al. |
| 2006/0240007 A1 | 10/2006 | Sanders |
| 2006/0276455 A1 | 12/2006 | Lindsberg et al. |
| 2007/0015813 A1 | 1/2007 | Carter et al. |
| 2007/0086981 A1 | 4/2007 | Meijer et al. |
| 2007/0093457 A1 | 4/2007 | Arber et al. |

(Continued)

FOREIGN PATENT DOCUMENTS

| | | |
|---|---|---|
| CA | 2408793 A1 | 12/2001 |
| CN | 101754746 A | 6/2010 |

(Continued)

OTHER PUBLICATIONS

Aisen et al., "Effects of rofecoxib or naproxen vs placebo on Alzheimer disease progression: a randomized controlled trial," JAMA, 289(21): 2819-2826 (2003).

(Continued)

*Primary Examiner* — Aradhana Sasan
(74) *Attorney, Agent, or Firm* — Foley Hoag LLP

(57) ABSTRACT

Methods of delivering cromolyn to a patient in need thereof, methods of treating amyloid-associated conditions and inflammatory or allergic lung diseases, and packs and kits comprising cromolyn are described.

28 Claims, No Drawings

(56) References Cited

U.S. PATENT DOCUMENTS

| | | |
|---|---|---|
| 2007/0107173 A1 | 5/2007 | Yamada |
| 2007/0178166 A1 | 8/2007 | Bernstein et al. |
| 2007/0193577 A1* | 8/2007 | Keller ............... A61K 9/0078 128/200.14 |
| 2007/0249644 A1 | 10/2007 | Pearson et al. |
| 2007/0293538 A1 | 12/2007 | Hobden |
| 2008/0021085 A1 | 1/2008 | Koo et al. |
| 2009/0110679 A1 | 4/2009 | Li et al. |
| 2009/0155256 A1 | 6/2009 | Black et al. |
| 2010/0113613 A1 | 5/2010 | McLaurin et al. |
| 2010/0143251 A1 | 6/2010 | Tamagnan et al. |
| 2010/0173960 A1 | 7/2010 | Cruz et al. |
| 2010/0234295 A1 | 9/2010 | Chen |
| 2010/0236550 A1 | 9/2010 | Zeng et al. |
| 2010/0266531 A1 | 10/2010 | Hsieh et al. |
| 2010/0298389 A1 | 11/2010 | Elmaleh et al. |
| 2011/0060138 A1 | 3/2011 | Elmaleh et al. |
| 2011/0129530 A1 | 6/2011 | Venkatesh et al. |
| 2011/0132434 A1 | 6/2011 | Correia et al. |
| 2011/0262442 A1 | 10/2011 | Hamilton et al. |
| 2012/0058049 A1* | 3/2012 | Elmaleh ............... A61K 31/352 424/1.89 |
| 2012/0082727 A1 | 4/2012 | Cocconi et al. |
| 2012/0118991 A1 | 5/2012 | Keller et al. |
| 2012/0121656 A1 | 5/2012 | Watson et al. |
| 2012/0134929 A1 | 5/2012 | McGrath et al. |
| 2012/0165366 A1 | 6/2012 | Ibrahim et al. |
| 2012/0175082 A1 | 7/2012 | Kmetovicz et al. |
| 2012/0308613 A1 | 12/2012 | Staniforth et al. |
| 2013/0197105 A1 | 8/2013 | Pipkin et al. |
| 2014/0140927 A1 | 5/2014 | Elmaleh et al. |
| 2014/0228304 A1 | 8/2014 | Jones et al. |
| 2015/0224077 A1 | 8/2015 | Gerhart et al. |
| 2015/0224078 A1 | 8/2015 | Gerhart et al. |
| 2015/0283113 A1 | 10/2015 | Elmaleh |
| 2016/0158150 A1 | 6/2016 | Morton et al. |
| 2016/0310503 A1 | 10/2016 | Elmaleh |
| 2017/0290797 A1 | 10/2017 | Elmaleh |
| 2018/0169277 A1 | 6/2018 | Elmaleh |
| 2018/0177789 A1 | 6/2018 | Elmaleh |
| 2018/0177790 A1 | 6/2018 | Elmaleh |
| 2018/0177791 A1 | 6/2018 | Elmaleh |
| 2018/0193491 A1 | 7/2018 | Elmaleh |
| 2018/0193492 A1 | 7/2018 | Elmaleh |
| 2018/0344682 A1 | 12/2018 | Elmaleh |
| 2019/0022006 A1 | 1/2019 | Elmaleh et al. |

FOREIGN PATENT DOCUMENTS

| | | |
|---|---|---|
| CN | 101848733 A | 9/2010 |
| EP | 1632242 A2 | 3/2006 |
| EP | 2322163 A1 | 5/2011 |
| EP | 2377860 A1 | 10/2011 |
| GB | 1144906 A | 3/1969 |
| GB | 1257162 A | 12/1971 |
| JP | S56-043448 B1 | 10/1981 |
| JP | 2001151673 A | 6/2001 |
| JP | 2005510535 A | 4/2005 |
| JP | 2005532091 A | 10/2005 |
| JP | 2007-534693 A | 11/2007 |
| JP | 2009-536918 A | 10/2009 |
| JP | 2010-510254 A | 4/2010 |
| JP | 2012-515712 A | 7/2012 |
| JP | 2012516356 A | 7/2012 |
| WO | WO-90/09789 A2 | 9/1990 |
| WO | WO-1997026934 A2 | 7/1997 |
| WO | WO-98/34596 A2 | 8/1998 |
| WO | WO-99/16422 A1 | 4/1999 |
| WO | WO-1999016422 A1 | 4/1999 |
| WO | WO-1999064095 A2 | 12/1999 |
| WO | WO-02/28820 A1 | 4/2002 |
| WO | WO-03/045331 A2 | 6/2003 |
| WO | WO-2005/104712 A2 | 11/2005 |
| WO | WO-2007/094718 A1 | 8/2007 |
| WO | WO-2007/102059 A1 | 9/2007 |
| WO | WO-2008/013799 A2 | 1/2008 |
| WO | WO-2008/061373 A1 | 5/2008 |
| WO | WO-2008/128981 A1 | 10/2008 |
| WO | WO-2008/131298 A2 | 10/2008 |
| WO | WO-2009/010770 A2 | 1/2009 |
| WO | WO-2009/133128 A1 | 11/2009 |
| WO | WO-2010/084767 A1 | 7/2010 |
| WO | WO-2010/088455 A2 | 8/2010 |
| WO | WO-2011/136754 A1 | 11/2011 |
| WO | WO-2014/066318 A1 | 5/2014 |
| WO | WO-2015/002703 A1 | 1/2015 |
| WO | WO-2015061397 A1 | 4/2015 |
| WO | WO-2016/196401 A1 | 12/2016 |
| WO | WO-2017091644 A1 | 6/2017 |
| WO | WO-2018/045217 A1 | 3/2018 |
| WO | WO-2019/199776 | 10/2019 |

OTHER PUBLICATIONS

Akiyama et al., "Inflammation and Alzheimer's Disease," Neurobiol Aging, 21(3): 383-421 (2000).

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

Aswania et al., "Relative bioavailability of sodium cromoglycate to the lung following inhalation, using urinary excretion," J Clin Pharmacol, 47:613-618 (1999).

Bannworth et al., "Stereoselective disposition of ibuprofen enantiomers in human cerebrospinal fluid," Br J Clin Pharmacol, 40(3):266-269 (1995).

Basek et al., "Efficacy of an Isotonic Small Droplet Size Nebulized DSCG on Asthma Control in Children," Acta Paediatrica, 99(Suppl 462):115 (2010).

Beach et al., "Cromolyn sodium toxicity studies in primates," Toxicol Appl Pharmacol, 57(3):367-400 (1981).

Berg et al., "Pharmaceutical salts," J Pharm Sci, 66(1):1-19 (1977).

Bodor et al., "Improved delivery through biological membranes VII. Dermal delivery of cromoglycic acid (cromolyn) via its prodrugs," International Journal of Pharmaceutics, 7(1):63-75 (1980).

Bot et al., "Perivascular mast cells promote atherogenesis and induce plaque destabilization in apolipoprotein E-deficient mice," Circulation, 115(19):2516-2525 (2007).

Breitner et al., "Extended results of the Alzheimer's disease anti-inflammatory prevention trial," Alzheimers Dement, 7(4):402-411 (2011).

Breitner, "Alzheimer disease: The changing view," Annals Neurol, 49(3):418-419 (2001).

Broe et al., "Anti-inflammatory drugs protect against Alzheimer disease at low doses," Arch Neurol, 57:1586-1591 (2000).

Bulic et al., "Tau protein and tau aggregation inhibitors," Neuropharmacology, 59: 276-289 (2010).

Byron et al., "Selection and Validation of Cascade Impactor Test Methods," Respiratory Drug Delivery IX, 1: 169-178 (2004).

Cacabelos, R., "Donepezil in Alzheimer's disease: From conventional trials to pharmacogenetics," Neuropsychiatric Disease and Treatment 2007:3(3), pp. 303-333 (2007).

Cairns, et al., "Synthesis and Structure-Activity Relationships of Disodium Cromoglycate and Some Related Compounds", Journal of Medicinal Chemistry, 15(6):583-589 (1972).

Chen et al., "Current experimental therapy for Alzheimer's Disease," Curr Neuropharmacol, 5(2): 127-134 (2007).

Cole et al., "Mechanisms of action of non-steroidal anti-inflammatory drugs for the prevention of Alzheimer's disease," CNS Neurol Disord Drug Targets, 9(2):140-148 (2010).

Cummings, "Alzheimer's Disease," N Engl J Med, 351(1):56-67 (2004).

(56) References Cited

OTHER PUBLICATIONS

Davies, "Clinical pharmacokinetics of ibuprofen. The first 30 years," Clin Pharmacokinet, 34(2):101-154 (1998).
Deiana, S. et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Alzheimer's and Dementia, 4( 4, Supplement):T499 (2008).
Doody et al., "Donepezil treatment of patients with MCI: a 48-week randomized, placebo-controlled trial," Neurology, 72(18):1555-1581 (2009).
Etminan et al., "Effect of non-steroidal anti-inflammatory drugs on risk of Alzheimer's disease: systematic review and meta-analysis of observational studies," Brit Med J, 327:128-131 (2003).
European Search Report for EP Application No. 13848340 dated Feb. 11, 2016.
European Search Report for European Application No. 14819448.3 dated Feb. 9, 2017.
Extended European Search Report for EP Application No. 16867341.6 dated Jun. 13, 2019.
Extended European Search Report, EP 10736439.0 dated Jun. 19, 2012.
Extended European Search Report, EP 14855211.0, dated May 29, 2017.
Findeis et al., "Design and testing of inhibitors of fibril formation," Methods Enzymol, 309:476-488 (1999).
Findeis et al., "Modified-peptide inhibitors of amyloid β-peptide polymerization," Biochemistry, 38(21):6791-6800 (1999).
Galimberti et al., "Disease-modifying treatments for Alzheimer's disease," Ther Adv Neurol Disord, 4(4): 203-216 (2011).
Garmise, "Novel Dry Powder Preparations of Whole Inactivated Influenza Virus for Nasal Vaccination," Dissertation, University of North Carolina at Chapel Hill (2007).
Gasparini et al., "Non-steroidal anti-inflammatory drugs (NSAIDs) in Alzheimer's disease: old and new mechanisms of action," J Neurochem, 91(3):521-536 (2004).
Gilani et al., "Influence of Formulation Variables and Inhalation Device on the Deposition Profiles of Cromolyn Sodium Dry Powder Aerosols," DARU vol. 12(3):123-130 (2004).
Griffin, "What causes Alzheimer's?" The Scientist, 25:36-40 (2011).
Guchardi, R. et al., "Influence of fine lactose and magnesium stearate on low dose dry powder inhaler formulations," International Journal of Pharmaceutics 348:10-17 (2008).
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mal Cell Biol, 8(2):101-112 (2007).
Hashimoto et al., "Apolipoprotein E, especially apolipoprotein E4, increases the oligomerization of amyloid β peptide," J Neurosci, 32(43):15181-15192 (2012).
Heneka et al., "Acute treatment with the PPARγ agonist pioglitazone and ibuprofen reduces glial inflammation and Aβ1-42 levels in APPV717I transgenic mice," Brain, 128:1442-1453 (2005).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hori et al., "A Food and Drug Administration-approved asthma therapeutic agent impacts amyloid β in the brain in a transgenic model of Alzheimer disease," J Biol Chem, 290(4):1966-1978 (2015).
Huang et al., "Acute stress induces cardiac mast cell activation and histamine release, effects that are increased in Apolipoprotein E knockout mice.," Cardiovasc Res, 55(1):150-160 (2002).

Huang et al., "Stress-induced interleukin-6 release in mice is mast cell-dependent and more pronounced in Apolipoprotein E knockout mice," Cardiovasc Res, 59(1):241-249 (2003).
Imbimbo et al., "Are NSAIDs useful to treat Alzheimer's disease or mild cognitive impairment?," Front Aging Neurosci, 2(Article 19):pp. 1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.
Intal Approval Package, Center for Drug Evaluation and Research, application 75-175, pp. 1-5 (Dec. 12, 1997).
International Search Report and Written Opinion for International Application No. PCT/US2013/066069 dated Mar. 13, 2014.
International Search Report and Written Opinion for International Application No. PCT/US16/63143 dated Feb. 6, 2017.
International Search Report and Written Opinion for International Application No. PCT/US16/63462 dated Feb. 1, 2017.
International Search Report and Written Opinion for International Application No. PCT/US17/65727 dated Feb. 12, 2018.
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report and Written Opinion for International Application No. PCT/US2019/026521 dated Jun. 14, 2019.
International Search Report for International Application No. PCT/US14/39118 dated Sep. 18, 2014.
Jin et al., "Mast cells are early responders after hypoxia-ischemia in immature rat brain," Stroke, 40(9):3107-3112 (2009).
Karran et al., "The amyloid cascade hypothesis for Alzheimer's disease: an appraisal for the development of therapeutics," Nat Rev, 10(9):698-712 (2011).
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).
Knowles et al., "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Koo et al., "Amyloid diseases: Abnormal protein aggregation in neurodegeneration, " PNAS, 96:9989-9990 (1999).
Kotilinek et al., "Cyclooxygenase-2 inhibition improves amyloid-β-mediated suppression of memory and synaptic plasticity," Brain, 131(3):651-664 (2008).
Koudstaal et al., "Secondary Stroke Prevention in Atrial Fibrillation: Indications, Risks, and Benefits," J Thromb Thrombolys, 7(1):61-65 (1999).
Krstic et al., "Deciphering the mechanism underlying late-onset Alzheimer disease," Nat Rev Neurol, 9:25-34(2013).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lanz et al., "The gamma-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice" The Journal of Pharmacology and Experimental Therapeutics, vol. 305(3):868-871 (2003).
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience 20(15):5709-5714 (2000).
Loeb et al., "A randomized, controlled trial of doxycycline and rifampin for patients with Alzheimer's disease," J Am Geriatr Soc, 52(3): 381-7 (2004).

(56) References Cited

OTHER PUBLICATIONS

Mackenzie et al., "Nonsteroidal anti-inflammatory drug use and Alzheimer-type pathology in aging," Neurology, 50(4):986-990 (1998).
Mandel, "CERE-110, an adeno-associated virus-based gene delivery vector expressing human nerve growth factor for the treatment of Alzheimer's disease," Curr Opin Mol Ther, 12(2): 240-247 (2010).
Marinkovic et al., "Evolution of Intracerebral Hemorrhage after Intravenous Tpa: Reversal of Harmful Effects with Mast Cell Stabilization," J Cerebr Blood F Met, 34(1):176-181 (2014).
Mash et al., "Loss of M2 muscarine receptors in the cerebral cortex in Alzheimer's disease and experimental cholinergic denervation," Science, 228(4703):1115-1117 (1985).
Mckittrick et al., "Mast Cells Promote Blood Brain Barrier Breakdown and Neutrophil Infiltration in a Mouse Model of Focal Cerebral Ischemia," J Cerebr Blood F Met, 35(4):638-647 (2015).
McLaurin et al., "Cyclohexanehexol inhibitors of Aβ aggregation prevent and reverse Alzheimer phenotype in a mouse model," Nat Med, 12(7):801-808 (2006).
Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mor et al., "Mast cells and atherosclerosis," Israel Med Assoc J, 3:216-221 (2001).
Morihara et al., "Ibuprofen Suppresses Interleukin-1beta Induction of Pro-Amyloidogenic alphal-Antichymotrypsin to Ameliorate beta-Amyloid (Abeta) Pathology in Alzheimer's Models," Neuropsychopharmacology 30:1111-1120 (2005).
Moss et al., "The absorption and clearance of disodium cromoglycate from the lung in rat, rabbit, and monkey," Toxicol Appl Pharmacol, 17(3):699-707 (1970).
Murphy, "Cromolyn sodium: basic mechanisms and clinical usage," Pediatric Asthma, Allergy, and Immunology, 2(4):237-254 (1988).
Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma—a critical review," Sleep Breath, 16:1027-1032 (2012).
Newman et al., "Therapeutic Aerosols 1—Physical and Practical Considerations," Thorax, 38(12): 881-886 (1983).
Obici et al., "AA amyloidosis: basic knowledge, unmet needs and future treatments, " Swiss Medical Weekly, 142:w13580 (2012).
Ono et al., "Push-pull benzothiazole derivatives as probes for detecting β-amyloid plaques in Alzheimer's brains," Bioorg Med Chem, 17(18):7002-7007 (2009).
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Panza et al., "Immunotherapy for Alzheimer's Disease: From anti-b-amyloid to tau-based Immunization strategies," Immunotherapy, 4(2):213-238 (2012).
Parepally et al., "Brain uptake of nonsteroidal anti-inflammatory drugs: ibuprofen, flurbiprofen, and indomethacin," Pharm Res, 23(5):873-881 (2006).
Petersen et al., "Vitamin E and donepezil for the treatment of mild cognitive impairment," N Engl J Med, 352(23):2379-2388 (2005).
Pratico, "Alzheimer's disease and non-steroidal anti-inflammatory drugs: Old therapeutic tools with novel mechanisms of action?" Current Medicinal Chemistry—Central Nervous System Agents 5(2):111-117 (2005).
Péhourcq et al., "Diffusion of arylpropionate non-steroidal anti-inflammatory drugs into the cerebrospinal fluid: a quantitative structure-activity relationship approach," Fundam Clin Pharmacol, 18(1):65-70 (2004).

Reagan-Shaw et al., "Dose Translation from Animal to Human Studies Revisited," The FASEB, 22: 659-661 (2007).
Reverchon et al., "Production of Cromolyn Sodium Microparticles for Aerosol Delivery by Supercritical Assisted Atomization," AAPS PharmSciTech 8(4) Article 114 (2007).
Richards et al., "Absorption and disposition kinetics of cromolyn sodium and the influence of inhalation technique," J Pharmacol Exp Ther, 241(3):1028-1032 (1987).
Rousselet et al., "Mouse Model of Intraluminal MCAO: Cerebral Infarct Evaluation by Cresyl Violet Staining," J Vis Exp, 69:e4038 (2012).
Sabbagh et al., "Latrepirdine, a potential novel treatment for Alzheimer's disease and Huntington's chorea," Curr Opin Investig Drugs, 11(1): 80-91 (2010).
Schnabel, J. "Early Results of Alzheimer's Passive Vaccine Trial Mixed," http://www.dana.org/News/Details.aspx?id=42815 printed Jan. 19, 2017, pp. 1-3 (2008).
Schneider et al., "Current Alzheimer's disease clinical trials: methods and placebo outcomes," Alzheimer's Dement, 5(5):388-397 (2009).
Shin et al., "Interpretation of Animal Dose and Human Equivalent Dose for Drug Development," Journal of Korean Oriental Medicine, 31: 1-7 (2010).
STN database CAS RN: 16110-51-3 (Nov. 16, 1984).
Strejan et al., "Suppression of chronic-relapsing experimental allergic encephalomyelitis in strain-13 guinea pigs by administration of liposome-associated myelin basic protein," J Neuroimmunol, 7(1):27-41 (1984).
Sun et al., "Mast cells promote atherosclerosis by releasing proinflammatory cytokines," Nat Med, 13(6):719-724 (2007).
Sun et al., "Synthesis of scyllo—inositol derivatives and their effects on amyloid beta peptide aggregation," Bioorganic & Medicinal Chemistry 16:7177-7184 (2008).
Tavemi et al., "Donepezil medicated memory improvement in traumatic brain injury during post acute rehabilitation," Brain Inj, 12(1):77-80 (1998).
Thal et al., "A randomized, double-blind, study of rofecoxib in patients with mild cognitive impairment," Neuropsychopharmacology, 30:1204-1215 (2005).
Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al, "Therapy of Alzheimer's disease: An update," African Journal of Pharmacy and Pharmacology, vol. 4(6):408-421 (2010).
Veld et al., "Nonsteroidal antiinflammatory drugs and the risk of Alzheimer's disease," N Engl J Med, 345:1515-1521 (2001).
Wang et al. "Allopregnanolone reverses neurogenic and cognitive deficits in mouse model of Alzheimer's disease," PNAS, 107(14): 6498-6503 (2010).
Weggen et al., "A subset of NSAIDs lower amyloidogenic A?42 independently of cyclooxygenase activity," Nature, 414(6860):212-216 (2001).
Wettstein et al., "Clinical trials with the cholinergic drug RS 86 in Alzheimer's disease (AD) and senile dementia of the Alzheimer type (SDAT)," Psychopharmacology, 84(4):572-573 (1984).
Yan et al., "Anti-inflammatory drug therapy alters β-amyloid processing and deposition in an animal model of Alzheimer's disease," J Neurosci, 23:7504-7509 (2003).
Zhang et al., "Cromolyn Reduces Levels of the Alzheimer's Disease-Associated Amyloid β-Protein by Promoting Microglial Phagocytosis," Sci Rep 8(1144) (2018).
Zhou et al., "Drug-lactose binding aspects in adhesive mixtures: controlling performance in dry powder inhaler formulations by altering lactose carrier surfaces," Adv Drug Deliv Rev, 64(3):275-284 (2012).
Zlokovic et al., "Neurovascular pathways to neurodegeneration in Alzheimer's disease and other disorders," Nat Rev Neurosci, 12(12):723-738 (2011).
Dunbar et al., "Dispersion and Characterization of Pharmaceutical Dry Powder Aerosols," Kona, 16:7-45 (1998).

(56) References Cited

OTHER PUBLICATIONS

Extended European Search Report for EP Application No. EP 16869210 dated Sep. 19, 2019.
Extended European Search Report for EP Application No. EP 19166810 dated Sep. 23, 2019.
Hirouchi, "Current status and perspectives on the deveolpment of therapeutic agents for Alzheimer's disease," Nihon Yakurigaku Zasshi, 123(6):421-427 (2004).
InnoPharmalabs, "Particle Size Distribution", Apr. 9, 2013 (Apr. 9, 2013).
International Search Report and Written Opinion for International Application No. PCT/US2019/40247 dated Sep. 20, 2019.
Notice of Allowance and Fees Due for U.S. Appl. No. 15/838,753, "Powdered Formulations of Cromolyn Sodium and Ibuprofen," dated Oct. 2, 2019.
Wikipedia, "Cromoglicic acid", Aug. 22, 2017 (Aug. 22, 2017), retrieved on Sep. 3, 2019 from https://en.wikipedia.org/w/index.php?title=Cromoglicic_acid&oldid=796733877.

* cited by examiner

CROMOLYN COMPOSITIONS AND METHODS THEREOF

CROSS-REFERENCE TO RELATED APPLICATIONS

This application is a continuation-in-part application of the U.S. patent application Ser. No. 14/893,487, filed Nov. 23, 2015, which is a national phase application of PCT international application PCT/US2014/039118, filed May 22, 2014, which claims priority to and the benefit of U.S. Provisional Application 61/826,798, filed May 23, 2013, both of which are incorporated by reference herein in their entirety.

FIELD OF THE INVENTION

The invention relates generally to cromolyn compositions and methods thereof. Specifically, the invention relates to effectively delivering cromolyn particles to a patient in need thereof for treating various diseases.

BACKGROUND OF THE INVENTION

Cromolyn (also known as cromoglicic acid, cromoglycate, or cromoglicate) has been approved previously for use in asthma. Its approved form is available as a disodium salt form, cromolyn sodium (also known as disodium cromoglycate or DSCG). Cromolyn demonstrates poor oral absorption. Delivery of cromolyn via inhalation has proven inefficient and difficult due, at least in part, to the hygroscopic nature of cromolyn sodium. For example, micronized powders containing cromolyn sodium particles spontaneously absorb water, forming clumps that impair efficient delivery of the cromolyn powder. See Keller et al. *Expert Opin. Drug Deliv.* 8, 1-17 (2011). Additionally, the performance and the efficiency of previously used inhalers are highly dependent upon a patient's inspiratory flow rate, leading to a wide variability in the amount of cromolyn sodium that is delivered to a patient. See Richards et al., Journal of Pharmacology and Experimental Therapeutics, 241, 1028-1032 (1987).

The present invention provides improved compositions and methods for delivering cromolyn via inhalation, efficiently and consistently over a range of inspiratory flow rates.

SUMMARY OF THE INVENTION

The invention is directed to a method of delivering cromolyn to a patient in need thereof. Such patients include patients in need of systemic delivery of cromolyn, e.g., to the brain or other non-lung tissues. In exemplary embodiments, the patient has an amyloid-associated condition. Patients in need of cromolyn also include patients in need of pulmonary delivery of cromolyn, for lung or airway related conditions. In exemplary embodiments, the patient has an inflammatory or allergic lung disease, such as asthma.

The method comprises administering to the patient via oral inhalation a pharmaceutically acceptable salt or ester of cromolyn in the form of a powder comprising particles of the pharmaceutically acceptable salt or ester of cromolyn. The majority of particles may have a diameter of about 2 to about 5 microns. The powder is administered using a device that deposits (a) at least 1.5 mg and (b) at least 20% by weight of the administered amount of pharmaceutically acceptable salt or ester of cromolyn to Stage 4 and higher of a Next Generation Pharmaceutical Impactor (NGI) cascade impactor device at a flow rate of, for example, 20-90 L/min.

In related methods, the invention also provides a method of delivering cromolyn to a patient in need thereof, comprising administering to the patient via oral inhalation a pharmaceutically acceptable salt or ester of cromolyn in the form of a powder, under conditions such that (a) at least 1.5 mg and (b) at least 20% by weight of the administered amount of the pharmaceutically acceptable salt or ester of cromolyn is delivered to the lower airways of the patient. As used herein, the term "lower airways" refers to the region of the airways/lung that corresponds to Stage 4 and higher of a Next Generation Pharmaceutical Impactor (NGI) cascade impactor device.

The invention also provides a method of delivering cromolyn to a patient in need thereof, comprising administering to the patient via oral inhalation a pharmaceutically acceptable salt or ester of cromolyn in the form of a powder comprising particles of the pharmaceutically acceptable salt or ester of cromolyn using a dry powder inhaler (DPI) device comprising a chamber comprising a piezoelectric vibrator or an ultrasonic vibrator for deaggregating a powder and an air flow passageway in which the deaggregated powder is picked up and carried for oral inhalation by a patient. The majority of the particles of the pharmaceutically acceptable salt or ester of cromolyn may have a diameter of about 2 to about 5 microns.

In various embodiments, about 3 mg to about 20 mg (e.g., about 16.1 mg to about 19.9 mg) of the pharmaceutically acceptable salt or ester of cromolyn is administered to the patient. Optionally the pharmaceutically acceptable salt or ester of cromolyn is administered with one or more pharmaceutically acceptable excipients. In various embodiments, the powder comprises about 0.1% to about 80%, for example, about 40% to about 80% by weight of an excipient. In various embodiments, the excipient is a monosaccharide, a disaccharide, an oligosaccharide, a polysaccharide, or a polyalcohol, such as lactose, mannitol, or sorbitol.

Additionally, the invention provides a method of treating an amyloid-associated condition in a patient in need thereof. The method comprises administering to the patient via oral inhalation an amount of powder comprising particles of a pharmaceutically acceptable salt or ester of cromolyn via pulmonary delivery, the majority of particles having a diameter of about 2 to about 5 microns, using a device that deposits (a) at least 1.5 mg and (b) at least 20% by weight of the administered amount of pharmaceutically acceptable salt or ester of cromolyn to Stage 4 and higher of a Next Generation Pharmaceutical Impactor (NGI) cascade impactor device at a flow rate of, for example, 20-90 L/min (e.g., for about 4 seconds).

The invention further provides a method of treating inflammatory or allergic lung diseases in a patient in need thereof. The method comprises administering to the patient via oral inhalation an amount of powder comprising particles of a pharmaceutically acceptable salt or ester of cromolyn, the majority of particles having a diameter of about 2 to about 5 microns, at a frequency of 1 or 2 times daily, each dose comprising about 3 mg to about 20 mg of a pharmaceutically acceptable salt or ester of cromolyn. The dose and/or frequency of delivery according to such methods are reduced compared to the conventional dosages and frequencies.

In various aspects of the invention, the powder comprising particles of a pharmaceutically acceptable salt or ester of cromolyn is administered to a patient using an active dry powder inhaler, such as a dry powder inhaler comprising a chamber comprising a piezoelectric vibrator or an ultrasonic vibrator for deaggregating a dry powder and an air flow passageway in which the deaggregated powder is picked up and carried for oral inhalation by a patient.

In various aspects, the invention is directed to a method for treating an amyloid-associated condition in a patient in need thereof, comprising administering to the patient via oral inhalation an amount of liquid particles of a solution comprising a pharmaceutically acceptable salt or ester of cromolyn using a nebulizer. The particles have a mass median aerodynamic diameter (MMAD) of about 0.5 to about 15 microns. In some embodiments, the majority of particles have a diameter of about 2 microns to about 5 microns.

The invention further includes use of a pharmaceutically acceptable salt or ester of cromolyn in the preparation of a medicament for treating inflammatory or allergic lung diseases in a patient in need thereof in an amount from about 3 mg to about 20 mg (e.g., from about 16.1 mg to about 19.9 mg). The medicament is administered via oral inhalation at a frequency of 1 or 2 times daily, and the pharmaceutically acceptable salt or ester of cromolyn is in the form of a powder comprising particles of pharmaceutically acceptable salt or ester of cromolyn optionally having a diameter of about 0.5 to about 15 microns, preferably an average particle size of about 5 microns or less. The invention further contemplates use of a pharmaceutically acceptable salt or ester of cromolyn in the preparation of a medicament for treating an amyloid-associated condition in a patient in need thereof. The medicament is administered to the patient via pulmonary delivery or oral inhalation. In some embodiments, the pharmaceutically acceptable salt or ester of cromolyn is in the form of a powder comprising particles of a pharmaceutically acceptable salt or ester of cromolyn, wherein the majority of particles having a diameter of about 2 to about 5 microns. The medicament is optionally delivered using a dry powder inhaler device as described herein. Alternatively, the pharmaceutically acceptable salt or ester of cromolyn is in solution and administered using a nebulizer.

Additionally, the invention provides a blister pack for delivering cromolyn to a patient in need thereof. The blister pack comprises blisters containing about 3 mg to about 20 mg (e.g., about 16.1 mg to about 19.9 mg) of a pharmaceutically acceptable salt or ester of cromolyn. The invention also is directed to a kit comprising a blister pack as described herein and a dry powder inhaler (DPI) device. In some embodiments, the device is an active dry powder inhaler, such as a dry powder inhaler device comprising a chamber comprising a piezoelectric vibrator for deaggregating a dry powder and an air flow passageway in which the deaggregated powder is picked up and carried for oral inhalation by a patient. In some embodiments, the kit further comprises ibuprofen tablets.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to specific embodiments described herein. The entire document is intended to be related as a unified disclosure, and it should be understood that all combinations of features described herein are contemplated, even if the combination of features are not found together in the same sentence, or paragraph, or section of this document. For example, where embodiments concerning a method of delivering cromolyn are described, embodiments involving methods of therapy, kits, and the like that have the same properties and features are specifically contemplated, and the reverse also is true.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to elements described as a selection within a range, it should be understood that all discrete subunits within the range are contemplated as an embodiment of the invention. Ranges may be expressed herein as from "about" or "approximately" one particular value and/or to "about" or "approximately" another particular value. When such a range is expressed, another embodiment according to the invention includes from the one particular value and/or to the other particular value. Similarly, when particular values are expressed as approximations, but use of antecedents such as "about," "at least about," or "less than about," it will be understood that the particular value forms another embodiment.

With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

DETAILED DESCRIPTION OF THE INVENTION

The invention provides improved methods and compositions for the efficient and consistent delivery of cromolyn via inhalation. Such methods preferably deliver a consistent amount of drug over a wide range of patient inspiratory flow rates. According to some aspects of the inventive method, a large portion of an administered amount of cromolyn is delivered to regions of the lungs that mediate transport into systemic circulation (the bronchi, bronchioles, and alveoli), e.g. the lower airways. Thus, the inventive method can provide an effective means for delivering cromolyn systemically, i.e., into the blood stream (and, by extension, to other non-lung regions of the body, such as the brain). The enhanced delivery efficiency associated with the inventive method allows administration of lower doses of cromolyn and/or less frequent administration of cromolyn, to achieve a desired biological response in any condition requiring lung delivery or systemic delivery. Advantages include improved therapeutic efficacy at conventional doses, or maintained/improved therapeutic efficacy at lower doses and/or lower frequencies of administration, leading to improved ease of use, higher patient compliance, and improved therapeutic benefit, as well as cost savings associated with using reduced amounts of drug. Additionally, many drug packaging systems containing groups of individual delivery units, such as blister packs or capsules, have maximum capacities for a single dose of drug contained within individual delivery units. More efficient delivery of cromolyn also advantageously facilitates the packaging of a therapeutically effective dose of cromolyn in each individual delivery unit. Advantages include delivery of a higher dose per single administration, delivery of uniform doses in a multiple administration regimen (i.e., little variability between doses), and/or use of a single individual delivery unit per administration rather than multiple individual delivery units per administration.

The invention is described in further detail below. Section headings are for convenience of reading and not intended to be limiting per se.

Powder Administration

In one aspect, the invention provides a method of delivering cromolyn to a patient in need thereof. Such patients include patients in need of lung or systemic delivery of cromolyn, and include patients with amyloid-associated conditions as well as patients with an inflammatory or allergic lung disease such as asthma. In any of the embodiments described herein, cromolyn (also known as cromoglicic acid, cromoglycate, cromoglicate, or 5,5'-(2-hydroxypropane-1,3-diyl)bis(oxy)bis(4-oxo-4H-chromene-2-carboxylic acid)) can be administered as a powder comprising particles of a pharmaceutically acceptable salt or ester of cromolyn.

Pharmaceutically acceptable salts are well known to those skilled in the art and include pharmaceutically acceptable inorganic and organic base addition salts, which may be formed with metals or amines, such as alkali and alkaline earth metals or organic amines. Pharmaceutically acceptable salts of compounds may also be prepared with a pharmaceutically acceptable cation. These salts can be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Suitable pharmaceutically acceptable cations are well known to those skilled in the art and include alkaline, alkaline earth, ammonium and quaternary ammonium cations. Examples of metals used as cations are lithium, sodium, potassium, magnesium, ammonium, calcium, aluminum, or ferric, and the like. Examples of suitable amines include ethylamine, diethylamine, piperazine, isopropylamine, trimethylamine, histidine, N,N'-dibenzylethylenediamine, chloroprocaine, choline, ethanolamine, diethanolamine, dicyclohexylamine, ethylenediamine, N-methylglucamine, and procaine. Suitable esters of cromolyn include, but are not limited to, carboxylate esters of one or both of the carboxylic acids of cromolyn, such as aliphatic esters (e.g., methyl esters, ethyl esters, propyl esters, butyl esters such as t-butyl esters, and pentyl esters), aryl esters (e.g., phenyl esters and benzyl esters), and combinations thereof. In one example, the pharmaceutically acceptable salt of cromolyn is disodium cromoglycate.

The pharmaceutically acceptable salt or ester of cromolyn is administered via inhalation, generally via oral inhalation, however, nasal inhalation or a combination of oral and nasal inhalation can also be used. When systemic delivery is desired, administration via inhalation as described herein delivers cromolyn to the lungs of the patient, depositing the pharmaceutically acceptable salt or ester of cromolyn onto surfaces of the lung that allow absorption into the blood stream (e.g., the bronchi, bronchioles, and alveoli), e.g. the lower airways.

In one embodiment, the particles of the cromolyn salt or ester have a median particle diameter ($D_{50}$) of less than about 5 microns, less than about 4.8 microns, less than about 4.5 microns, less than about 4.2 microns, less than about 4 microns, less than about 3.8 microns, less than about 3.5 microns, less than about 3.2 microns, less than about 3 microns, less than about 2.8 microns, less than about 2.5 microns, less than about 2 microns, less than about 1.8 microns, less than about 1.5 microns, less than about 1.2 microns, less than about 1 micron, about 0.1 microns to about 5 microns, about 0.5 microns to about 5 microns, about 0.8 microns to about 5 microns, about 1 micron to about 5 microns, about 1.2 microns to about 5 microns, about 1.5 microns to about 5 microns, about 1.8 microns to about 5 microns, about 2 microns to about 5 microns, about 1.2 microns to about 5 microns, about 2.5 micron to about 5 microns, about 2.8 microns to about 5 microns, about 3 microns to about 5 microns, about 3.2 microns to about 5 microns, 3.5 micron to about 5 microns, about 3.8 microns to about 5 microns, about 4 microns to about 5 microns, about 4.2 microns to about 5 microns, 4.5 micron to about 5 microns, and/or about 4.8 to about 5 microns. The particles of the cromolyn salt or ester optionally have a $D_{90}$ of less than 15 microns, less than 14 microns, less than 13 microns, less than 12 microns, less than 11 microns, less than 10 microns, less than 9.5 microns, less than 9 microns, less than 8.5 microns, less than 8 microns, less than 7.5 microns, less than 7 microns, less than 6.5 microns, less than 6 microns, less than 5.5 microns, less than 5 microns, less than 4.5 microns, less than 4 microns, less than 3.9 microns, less than 3.8 microns, less than 3.7 microns, less than 3.6 microns, about 3 microns to about 15 microns, about 5 microns to about 13 microns, about 7 microns to about 11 microns, and/or about 9 microns to about 10 microns.

As used herein, the term $D_{50}$ refers to a diameter at which 50% of a sample's mass is comprised of smaller particles. As used herein, the term $D_{90}$ refers to a diameter at which 90% of a sample's mass is comprised of smaller particles. The D50 is also known as the "mass median diameter" as it divides the sample equally by mass.

In another embodiment, the particles of the cromolyn salt or ester have a mass median aerodynamic diameter (MMAD) of about 0.5 to about 15 microns, about 0.5 to about 10 microns, about 1 to about 5 microns, about 1 to about 4 microns, about 1 to about 3.5 microns, about 1 to about 3 microns, about 1 to about 2.5 microns, and/or about 1 to about 2 microns. Particles of a desired size are obtained by any method, such as a method known to one of skill in the art, including micronization or milling. As used herein, the term "aerodynamic diameter" refers to the diameter of a sphere of unit density that reaches the same velocity in an air stream as a non-spherical particle of arbitrary density. As used herein, the term "mass median aerodynamic diameter" refers to the aerodynamic diameter at which 50% of the particles by mass are larger and 50% are smaller. Methods of determining aerodynamic diameter are known in the art and described in, e.g., Chow et al., "Particle Engineering for Pulmonary Drug Delivery," Pharm. Res., 24 (3), 411-437 (2007).

The particles of the cromolyn salt or ester may have a geometric standard deviation (GSD) of about 1.3 to about 2.5, about 1.4 to about 2.4, about 1.5 to about 2.3, about 1.6 to about 2.2, about 1.7 to about 2.1, and/or about 1.8 to about 2. As used herein, the term "geometric standard deviation" refers to the spread of an aerodynamic particle size distribution. GSD can be calculated as follows: $GSD=(d_{84}/d_{16})^{1/2}$, where $d_{84}$ and $d_{16}$ represent the diameters at which 84% and 16% of the aerosol mass are contained, respectively, in diameters less than these diameters.

The powder optionally comprises one or more pharmaceutically acceptable excipients. Suitable excipients are well tolerated by pulmonary tissue, and include, but are not limited to, monosaccharides, disaccharides, oligosaccharides, polysaccharides, polyalcohols, and combinations thereof. Exemplary excipients include, but are not limited to, lactose, mannitol, sorbitol, and combinations thereof. The pharmaceutically acceptable excipient(s), when present, are included in the powder in a total amount of about 0.1% to about 80% by weight, about 1% to about 80% by weight, about 5% to about 80% by weight, about 10% to about 80% by weight, about 15% to about 80% by weight, about 20% to about 80% by weight, about 25% to about 80% by weight, about 30% to about 80% by weight, about 35% to about 80% by weight, about 40% to about 80% by weight, about 20% to about 75% by weight, about 20% to about 70% by weight, about 20% to about 65% by weight, about 20% to about 60% by weight, about 25% to about 55% by weight, about 30% to about 50% by weight, about 35% to about 45% by weight, and/or about 40% by weight. The pharmaceutically acceptable excipients can be included in an anhydrous form or as a hydrate, such as a monohydrate or higher-order hydrate. The excipient(s) optionally have a particle size of about 250 microns or less, such as about 10 microns to about 150 microns, although other excipient particle sizes may be used in the context of the invention.

A particular administration regimen for a particular patient will depend on several factors, such as the condition being treated, co-therapies administered, the size of the patient, frequency of administration, etc. In various embodiments, the amount of powder that is administered to a patient comprises about 3 mg to about 20 mg of the pharmaceutically acceptable salt or ester of cromolyn, for example, about 3 mg to about 19 mg, about 3 mg to about 18 mg, about 3 mg to about 17 mg, about 3 mg to about 16 mg, about 3 mg to about 15 mg, about 3 mg to about 14 mg, about 3 mg to about 13 mg, about 3 mg to about 12 mg, about 3 mg to about 11 mg, about 3 mg to about 10 mg, about 3 mg to about 9 mg, about 3 mg to about 8 mg, about 3 mg to about 7 mg, about 4 mg to about 20 mg, about 6 mg to about 19 mg, about 8 mg to about 18 mg, about 10 mg to about 18 mg, about 12 mg to about 18 mg, about 14 mg to about 18 mg, about 16 mg to about 18 mg, about 17 mg to about 18 mg, about 16.1 mg to about 19.9 mg, or 16.1 mg to 19.9 mg of the pharmaceutically acceptable salt or ester of cromolyn. The amount of powder is optionally administered as a single dose or administration, which may be inhaled in a single breath or span multiple breaths in the course of the single administration. Optionally, the single dose or administration is administered from a single individual delivery unit, such as a single blister or single capsule. This single dose (single administration) may be administered repeatedly to the patient at any interval over the course of a treatment period. For example, a single dose of pharmaceutically acceptable salt or ester of cromolyn (e.g., about 16.1 mg to about 19.9 mg) is administered to a patient once a day, twice a day, or three times a day for a treatment period. Examples of treatment periods include at least 1, 2, 3, 4, 5, 6, or 7 days, or at least 1, 2, 3, or 4 weeks, or at least 1, 2, 3, 4, 5 or 6 months, or a year or more.

Generally, administering the powder involves suspending the powder into a gas (such as air or oxygen), thereby forming an aerosol containing the powder and the gas. Concurrently with, or subsequent to, suspension formation, the powder suspension is inhaled by a patient. In some embodiments, the powder is suspended in a gas stream being inhaled by a patient such that administering comprises suspending the powder into an inhaled gas stream.

Suspending the powder into a gas (such as air or oxygen) may be carried out by any means, including vibration. Vibrating the powder generally aerosolizes at least a portion (i.e., at least about 10%, at least about 30%, at least about 50%, at least about 75%, and/or at least about 90%) of the powder. For example, vibrating the powder generally involves suspending at least a portion of the powder in the gas that is in the immediate vicinity of the powder. Additionally, the powder comprising particles of cromolyn and optional pharmaceutically acceptable excipient(s) can include aggregates, for example, aggregates between two or more cromolyn particles and/or between cromolyn particles and excipient particles. Without intending to be bound by any particular theory, vibrating the powder deagglomerates particle aggregates, advantageously providing smaller particles that are more readily delivered regions of the lungs allowing transport into the blood stream (e.g., the bronchi, bronchioles, and alveoli), e.g. the lower airways. Optionally, the vibrator is vibrated such that the resulting vibrations generate synthetic jets that aerosolize and/or deaggregate the powder. Methods for forming synthetic jets are described, for example, in U.S. Pat. No. 7,318,434, which is incorporated herein by reference in its entirety. Preferably, administering the powder involves vibrating the powder at high frequency, for example, a frequency of about 10 kHz to about 50 kHz, about 15 kHz to about 40 kHz, and/or about 20 kHz to about 30 kHz.

In some embodiments of the invention, the amount of powder comprising particles of a pharmaceutically acceptable salt or ester of cromolyn is administered using a device that deposits (a) at least 1.5 mg and (b) at least 20% by weight of the administered amount of pharmaceutically acceptable salt or ester of cromolyn to Stage 4 and higher of a Next Generation Pharmaceutical Impactor (NGI) cascade impactor device at a flow rate of, for example, 20-90 L/min for about 1 to about 10 seconds (e.g., for about 4 seconds). In exemplary embodiments, the device deposits (a) at least 1 mg, at least 1.5 mg, at least 1.8 mg, at least 2 mg, at least 2.2 mg, at least 2.5 mg, at least 2.8 mg, at least 3 mg, at least 3.2 mg, at least 3.5 mg, at least 3.8 mg, at least 4 mg, at least 4.2 mg, at least 4.5 mg, at least 4.8 mg, at least 5 mg, at least 5.2 mg, at least 5.5 mg, at least 5.8 mg, at least 6 mg, at least 6.2 mg, at least 6.5 mg, at least 6.8 mg, at least 7 mg, at least 7.2 mg, at least 7.5 mg, at least 7.8 mg, at least 8 mg, at least 8.2 mg, at least 8.5 mg, at least 8.8 mg, at least 9 mg, at least 9.2 mg, at least 9.5 mg, at least 9.8 mg, at least 10 mg, about 1.3 mg to about 7 mg, about 1.5 mg to about 3 mg, about 1.5 mg to about 5 mg, about 1.5 mg to about 7 mg, about 1 mg to about 4 mg, about 1 mg to about 5 mg, about 1 mg to about 7 mg, about 1.8 mg to about 5.8 mg, about 1.5 mg to about 5.5 mg, and/or about 2 mg to about 5 mg and (b) at least 10%, at least 20%, at least 30%, at least 35%, at least 40%, at least 45%, about 30% to about 75%, about 30% to about 65%, about 30% to about 60%, about 30% to about 55%, and/or about 30% to about 50% by weight of the administered amount of pharmaceutically acceptable salt or ester of cromolyn to Stage 4 and higher of an NGI cascade impactor device at a flow rate of, for example, 20 L to 90 L/min for about 10 seconds or less. As used herein, the term "administered amount" in the phrase "% by weight of the administered amount" refers to the amount of pharmaceutically acceptable salt or ester of cromolyn present in the individual delivery unit (e.g., blister or capsule or other unit dose container) connected to the device. Thus, in one illustrative embodiment, the device delivers at least about 4 to about 5 mg of cromolyn salt or ester to Stage 4 and higher of an NGI cascade impactor as described herein from a capsule or blister comprising, for example about 17.1 mg, of cromolyn salt or ester with or without added excipients. NGI cascade impactors are useful for studying aerodynamic size distribution of aerosols and simulating delivery to different regions of the lung. The respiratory tract forms a particle size-selective system wherein progressively finer particles pass through mouth, larynx and larger airways to be deposited in the peripheral lung (e.g., the alveolar spaces). Similarly, cascade impactors include several "stages" allowing passage of progressively finer particles through the system. An aerosol stream carrying particles passes through each stage at a constant air flow (e.g., 20-90 L/min). Particles of similar aerodynamic size deposit at a particular stage; smaller particles are deposited at further stages of the NGI cascade impactor than larger particles. In one example, at a flow rate of 70-90 L/min (e.g., for about 4 seconds of total actuation), Stages 4 and higher of the NGI cascade impactor trap particles having a mass median aerodynamic diameter (MMAD) of about 5 microns or less. The NGI cascade impactor is generally operated under conditions of low relative humidity, such as 20% relative humidity or less. Deposition in the central (bronchial) region of the lung generally peaks with particles having an MMAD of about 4 to about 6 microns, and deposition in the peripheral (alveolar) region of the lung generally peaks with particles having an MMAD of about 2 to about 4 microns. See Mitchell and Nagel, "Particle Size Analysis of Aerosols from Medicinal Inhalers," KONA, 22, 32-65 (2004). Thus, Stages 4 and higher of the NGI cascade impactor at a flow rate of 70-90 L/min (e.g., for about 4 seconds of total actuation) simulate the regions of the lung providing significant systemic absorption of a medicament into the bloodstream. NGI cascade impactor devices are available from MSP Corporation, Shoreview, Minn.

Advantageously, the inventive methods for delivering cromolyn allow consistent delivery of the active agent over a wide range of flow rates. For example, a consistent amount of powder is delivered to a patient over an inhalation flow rate of 20 L/min to 100 L/min, or 20 to 80 L/min, 20 to 60 L/min, 40-80 L/min, 60-80 L/min, 60-90 L/min, 70-90 L/min, or 75-85 L/min. By "consistent amount" is meant a relative standard deviation (RSD) of 10% or less (e.g., 5% or less, 3% or less and/or 2.5% or less) in the amount powder that is received by the patient.

Devices for Powder Administration

The devices for administering the powder described herein include, but are not limited to, a dry powder inhaler (DPI) device, a metered dose inhaler (MDI) device, and a dry powder nebulizer (DPN) device. Suitable devices typically administer a metered dose or a predetermined dose. Such doses generally are administered over a set period of time or a set volume of air. In various embodiments, the device functions independent of the patient's inspiratory flow rate. Thus, for example, the device delivers a consistent amount of cromolyn over a wide range of flow rates, such as an inhalation flow rate of 20 L/min to 100 L/min, or 20 to 80 L/min, 20 to 60 L/min, 40-80 L/min, 60-80 L/min, 60-90 L/min, 70-90 L/min, or 75-85 L/min. In a particular embodiment, the device delivers a consistent amount of cromolyn at an inhalation flow rate of 80 L/min.

Optionally, the device is a dry powder inhaler comprising a chamber in fluid communication with an air flow passageway. Included in the chamber is a vibrator, e.g., a piezoelectric vibrator or an ultrasonic vibrator, suitable for aerosolizing and/or deaggregating a dry powder. The inhaler optionally includes a lever for activating the piezoelectric or ultrasonic vibrator and for cooperating with a means for puncturing a blister or opening means for opening a blister.

In one embodiment, powder is delivered from the inhaler by receiving a pack (e.g., capsule or blister) containing the powder in an operating position proximal to the piezoelectric or ultrasonic vibrator. The patient places the mouthpiece of the inhaler into the mouth, forms a seal with his/her lips around the mouthpiece, and withdraws air through the air flow passageway while pressing the lever. Upon activation by the lever or other triggering event, the pack is broken, the piezoelectric or ultrasonic vibrator is activated, and the deaggregated powder is picked up into the inspiratory air flow of the patient and carried through the air flow passageway for inhalation by the patient.

The inhaler optionally includes an inhalation flow rate detector which detects the movement of air through the air flow passageway. In some embodiments, when the inhaler includes an inhalation flow rate detector, the event that triggers release of the powder includes movement of air through the air flow passageway above a threshold rate.

In some embodiments, the powder is delivered in a period of time of, for example, about one second to about five seconds of total inhalation time, for example, about one second to about two seconds. The inhalation period can be monitored using a visual indicator, e.g., flashing or changing the color of a light emitting diode, or an audible indicator.

Optionally, the lever, inhalation flow rate, and piezoelectric or ultrasonic vibrator functions are monitored and recorded in memory, such as a flash drive or other computer memory in direct contact with the inhaler or removed from the inhaler but in signal communication with the inhaler. For example, the functional parameters of the device may be transmitted from the device to a remote location, recorded in memory, and made available to healthcare providers via a wired or wireless communication network. The information also optionally may be delivered to point of care devices for monitoring treatment. The recorded performance information allows health care practitioners to monitor the use of the device, which can be particularly beneficial when a patient's ability to operate the device diminishes due to declining cognitive and/or physical health.

Devices also are described in U.S. Pat. Nos. 6,026,809, 7,318,434, 7,334,577, 7,779,837, 8,322,338, and 8,371,294, U.S. Patent Application Publication Nos. 2009/0090361, 2010/0294278, 2012/0077786, International Application Publication No. WO 2005/076872, and European Patent No. 0591136 B1, which are incorporated by reference in their entireties.

Solution Administration Using a Nebulizer

In various embodiments, the invention also includes a method comprising administering cromolyn to a patient using a nebulizer, preferably in a method for treating an amyloid-associated condition in a patient in need thereof. The method comprises administering liquid particles of a solution comprising a pharmaceutically acceptable salt or ester of cromolyn using a nebulizer via inhalation (e.g., oral inhalation) by the patient. These solution particles are droplets of solution in which the pharmaceutically acceptable salt or ester of cromolyn and any optional excipients are dissolved. The pharmaceutically acceptable salt or ester of cromolyn can be present in the solution at a concentration of about 1 mg/mL to about 100 mg/mL, for example, about 5 mg/mL to about 50 mg/mL, and/or about 10 mg/mL to 20 mg/mL. When included, excipient(s) can be present in the solution at a concentration of about 1 mg/mL to about 100 mg/mL, for example, about 5 mg/mL to about 50 mg/mL, and/or about 10 mg/mL to 20 mg/mL. The solution particles (i.e., droplets) have a mass median aerodynamic diameter (MMAD) of about 1 micron to about 10 microns, for example, about 1 micron to 8 micron, about 1 micron to 4 micron, about 1 micron to about 3.5 microns, about 1 micron to about 3 microns, about 1 micron to about 2.5 microns, about 1 micron to about 2 microns, about 2 microns to about 4 microns, and/or about 2.5 microns to about 3.5 microns. The solution particles (i.e., droplets) also optionally comprise a median diameter of less than about 2 microns, less than about 1.8 microns, less than about 1.5 microns, less than about 1.2 microns, less than about 1 micron, about 0.5 microns to about 2 microns, about 0.8 microns to about 2 microns, about 1 micron to about 2 microns, about 1.2 microns to about 2 microns, about 1.5 microns to about 2 microns, and/or about 1.8 microns to about 2 microns. Excipients, dosage, target regions of the lung, delivery amounts and efficiencies, and methods of estimating delivery to target regions of the lung are described above.

Suitable devices for administering cromolyn as a solution include, but are not limited to, a jet, ultrasonic or electronic nebulizers. Such nebulizer devices form aerosolized particles of cromolyn (e.g., a pharmaceutically acceptable salt or ester of cromolyn, such as cromolyn sodium) from a pharmaceutically acceptable solution (e.g., a hypotonic or isotonic solution). The nebulizer device optionally includes a liquid reservoir separated from a mouthpiece or face mask by a vibrating mesh, a piezoelectric element, or a compressed gas atomizer element. In such arrangements, a solution comprising a pharmaceutically acceptable salt or ester of cromolyn is present in the liquid reservoir, and the device produces a mist of particles for oral inhalation. When using a nebulizer, the cromolyn solution is optionally delivered to the patient via inhalation (oral, nasal, or a combination thereof) over the course of about ten minutes or less (e.g., two minutes).

The nebulizer may have any of the features of dry powder administration devices described herein. In exemplary embodiments, the device deposits/delivers at least 1 mg, at least 1.5 mg, at least 1.8 mg, at least 2 mg, at least 2.2 mg, at least 2.5 mg, at least 2.8 mg, at least 3 mg, at least 3.2 mg, at least 3.5 mg, at least 3.8 mg, at least 4 mg, at least 4.2 mg, at least 4.5 mg, at least 4.8 mg, at least 5 mg, at least 5.2 mg, at least 5.5 mg, 5.8 mg, at least 6 mg, at least 6.2 mg, at least 6.5 mg, at least 7.8 mg, at least 7 mg, at least 7.2 mg, at least 7.5 mg, 7.8 mg, at least 8 mg, at least 8.2 mg, at least 8.5 mg, at least 8.8 mg, at least 9 mg, at least 9.2 mg, at least 9.5 mg, at least 9.8 mg, at least 10 mg, about 1.3 mg to about 7 mg, about 1.5 mg to about 3 mg, about 1.5 mg to about 5 mg, about 1.5 mg to about 7 mg, about 1 mg to about 4 mg, about 1 mg to about 5 mg, about 1 mg to about 7 mg, about 1.8 mg to about 5.8 mg, about 1.5 mg to about 5.5 mg, and/or about 2 mg to about 5 mg of pharmaceutically acceptable salt or ester of cromolyn to Stage 4 and higher of an NGI cascade impactor device at a flow rate of, for example, 20 L to 90 L/min for about 10 seconds or less. In exemplary embodiments, the device deposits/delivers at least 20%, at least 30%, at least 35%, at least 40%, at least 45%, about 30% to about 75%, about 30% to about 65%, about 30% to about 60%, about 30% to about 55%, and/or about 30% to about 50% by weight of the administered amount of pharmaceutically acceptable salt or ester of cromolyn (as defined above) to Stage 4 and higher of an NGI cascade impactor device at a flow rate of, for example, about 20 L to about 90 L/min (e.g., for about 10 seconds or less).

Nebulizers also are described in U.S. Pat. No. 8,263,645 and U.S. Patent Application Publication Nos. 2007/0193577, 2009/0118249, and 2012/0118991, which are incorporated by reference in their entireties.

Amyloid-Associated Conditions

Any of the methods described herein include a method of treating an amyloid-associated condition in a patient in need thereof. In various example embodiments, the method comprises administering to the patient via inhalation an amount of powder comprising particles of a pharmaceutically acceptable salt or ester of cromolyn as described herein. As described above, in alternative embodiments, the method comprises administering to the patient via inhalation an amount of particles of a solution comprising a pharmaceutically acceptable salt or ester of cromolyn using a nebulizer.

Without wishing to be bound by a particular theory, disodium cromolyn penetrates the blood-brain barrier to bind beta-amyloid peptides and inhibit association of amyloid peptides and/or polymerization into oligomers and higher order aggregates. The inhibition of beta-amyloid association and/or polymerization is believed to arrest amyloid-mediated impairment of neurons and may enhance removal of oligomers and/or aggregates from the brain, thereby slowing, stopping or reducing amyloid accumulation in the brain.

By "amyloid-associated condition" is meant a disease or pathological disorder associated with abnormal amyloid aggregation and/or accumulation. See Eisenberg and Jucker, Cell, 148, 1188-1203 (2012). Amyloid accumulation has been linked to a wide variety of disorders ranging from neurodegenerative disorders to systemic amyloidoses to arthritis. Examples of amyloid-associated conditions include, but are not limited to, Alzheimer's disease (beta amyloid), dementia, diabetes mellitus type 2 (IAPP), Parkinson's disease (alpha-synuclein), idiopathetic myeloma, amyloid polyneuropathy, amyloid cardiomyopathy, systemic senile amyloidosis, transmissible spongiform encephalopathy (e.g., Creutzfeldt-Jakob disease) (PrPSc), Down's syndrome, Huntington's Disease (Huntingtin), medullary carcinoma of the thyroid (calcitonin), atherosclerosis (apolipoprotein), rheumatoid arthritis (serum amyloid A), aortic medial amyloid (Medin), prolactinomas (prolactin), familial amyloid polyneuropathy (FAP) (transthyretin), frontemporal lobar degeneration-tau (Tau), Familial British and Danish dementia (BriPP), hereditary non-neuropathic systemic amyloidosis (lysozyme), dialysis-related amyloidosis (beta 2 microglobulin), Finnish amyloidosis (Gelsolin), atrial amyloidosis (atrial natriuretic factor), transthyretin familial amyloidosis (TTR), hereditary fibrinogen alpha-chain amyloidosis (fibrinogen alpha-chain), motor neuron diseases, lattice corneal dystrophy (keratoepithelin), amyotrophic lateral sclerosis (SOD1), and cerebral amyloid angiopathy (beta amyloid, cystatin). See, e.g., Koo et al., PNAS, 96(18), 9989-9990 (1999); Eisenberg and Jucker, supra. Other examples of amyloid-associated conditions include head injuries (traumatic brain injury); amyloid-β plaques have been found in patients within hours following traumatic brain injury. See Johnson et al., Nature Reviews Neuroscience, 11, 361-370 (2010).

As used herein, "treating" and "treatment" refers to any reduction in the severity and/or onset of signs or symptoms associated with an ailment, such as an amyloid-associated condition or an inflammatory or allergic lung disease (described below). Accordingly, "treating" and "treatment" includes therapeutic and prophylactic measures that reduce any of the signs or symptoms. One of ordinary skill in the art will appreciate that any degree of protection from, or amelioration of, an amyloid-associated condition or symptom associated therewith is beneficial to a subject, such as a human patient. For example, a reduction in signs such as detectable amyloid plaques can be beneficial. In another example, an increase in soluble amyloid levels in the cerebrospinal fluid from abnormally low levels to normal, age-appropriate levels can also be beneficial. The quality of life of a patient is improved by reducing to any degree the severity of symptoms in a subject and/or delaying the appearance of symptoms. Accordingly, the method in one aspect is performed as soon as possible after it has been determined that a subject is at risk for an amyloid-associated condition or as soon as possible after the amyloid-associated condition manifests in the subject. For example, due to the rapid development of amyloid-β plaques in traumatic brain injury patients, prognosis may be improved by initiating treatment as soon as possible after the occurrence of the head injury.

Detection of a risk, onset, or presence of amyloid-associated condition is performed using any of a number techniques. Amyloid deposits can be detected ex vivo using, e.g., fluorescent dyes, circular dichroism, and X-ray diffraction. For example, amyloids in biopsied tissue typically demonstrate green birefringence when stained with Congo red and viewed under a polarizing microscope. Amyloid plaques can be detected in vivo using, e.g., magnetic resonance imaging (MRI) (see, e.g., Baltes et al., Methods Mol Biol., 711, 511-33 (2011)) and positron emission tomography (PET) (Kepe et al., Methods Enzymol., 412, 144-60 (2006)). Many of the neurodegenerative diseases referenced herein also are diagnosed by conducting mental status and neuropsychological tests (assessing, e.g., memory and problem solving) and blood tests (e.g., blood tests for Alzheimer's disease biomarker signatures). See Burnham et al., "A blood-based predictor for neocortical Aβ burden in Alzheimer's disease: results from the AIBL study," Molecular Psychiatry (April 2013).

Inflammatory or Allergic Lung Diseases

The invention provides methods of treating inflammatory or allergic lung diseases in a patient in need thereof, comprising administering to the patient via inhalation an amount of powder comprising particles of a pharmaceutically acceptable salt or ester of cromolyn as described herein. The dose and/or frequency of administration according to such methods are reduced compared to the conventional dosages and frequencies.

Inflammatory or allergic lung diseases include asthma, chronic obstructive pulmonary disease (COPD), acute respiratory distress syndrome (ARDS), pulmonary fibrosis, cystic fibrosis. Asthma, for example, is a condition associated with inflammation of airway passages in the lungs and airway hyperresponsiveness (AHR). Asthma also is marked by excess mucus production. Symptoms range from minor (e.g., slight shortness of breath) to severe (wheezing, inability to breath, and/or chest tightness) and vary from person to person. During an asthma attack, the lining of airways swell, thereby constricting the passage and reducing airflow to and from the lungs. Asthma is caused or triggered by, for example, infection, allergens, chemical substances and fumes, pollutants, medications, physical exertion, stress, and food additives. Asthma is classified into four general categories: mild intermittent (mild symptoms up to two days/week), mild persistent (symptoms more than twice/week, but not daily, and one or two nighttime episodes/month), moderate persistent (daily symptoms and three or four nighttime symptoms/month), and severe persistent (symptoms throughout most days and frequently at night).

As described herein, "treating" and "treatment" refers to any reduction in the severity and/or onset of symptoms associated with inflammatory or allergic lung diseases (e.g., asthma) and, as such, includes therapeutic and prophylactic measures. For example, treatment may result in a reduced number and/or severity of asthmatic attacks in a patient prone to allergy or airway hyperresponsiveness. The method in one aspect is performed as soon as possible after it has been determined that a subject is at risk for inflammatory or allergic lung diseases (e.g., allergy or airway hyperresponsiveness is diagnosed) or as soon as possible after an inflammatory or allergic lung disease (e.g., asthma) manifests in the subject.

Combination Therapies

The pharmaceutically acceptable salt or ester of cromolyn is optionally administered with one or more additional medicaments. For example for amyloid-associated conditions, additional anti-amyloid agents or anti-inflammatory agents can be administered. For inflammatory or allergic lung diseases, additional anti-asthma agents, or anti-inflammation agents, or other agents that are used to treat airway hyperresponsiveness can be administered.

Additional medicaments may be provided in any dosage form, including solid dosage forms (e.g., tablets, capsules and powders) and liquid dosage forms (e.g., solutions, suspensions, emulsions, syrups and elixirs). The additional medicaments may be administered by any known route of administration, including oral (e.g., ingestion or inhalation), injection (e.g., intravenous, intraarterial, intramuscular, subcutaneous, intradermal, intraarticular, intrathecal, epidural, intracerebral, or intraperitoneal), buccal, rectal, topical, transdermal, intranasal, via the pulmonary route, via inhalation, or intraophthalmic. The additional medicaments may be administered concurrently with or sequentially (i.e. before or after) with the pharmaceutically acceptable salt or ester of cromolyn.

Additional medicaments include, for example, Levodopa (Sinemet), anticholinergics, Eldepryl, steroids, antihistamines, long-acting or short-acting beta-agonists, immunomodulators (e.g., Omalizumab), and Theophylline.

In the case of amyloid-associated conditions, the additional medicament can be a cholinesterase inhibitor (e.g., Donepezil (Aricept®), rivastigmine (Exelon®), galantamine (Razadyne®), or Tacrine (Cognex®)), a NMDA receptor antagonist (e.g., memantine (Namenda®)), a gamma secretase inhibitor (e.g., LY451039 (Semagacestat, Eli Lily)), a metal ionophore (e.g., PBT2 (Prana)), a statin, and/or an endocannabinoid (e.g., arachidonoylethanolamine, tetrahydrocannabinol, 2-arachidonoyl glycerol, 2-arachidonyl glyceryl ether, N-arachidonoyl-dopamine, or virodhamine). Examples of non-steroidal anti-inflammatory drugs, include, but are not limited to, ibuprofen, acetylsalicylic acid, diflunisal, salsalate, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, licofelone, hyperforin, and figwort. Preferably, the non-steroidal anti-inflammatory drug is administered orally (via ingestion or inhalation). The non-steroidal anti-inflammatory drug (e.g., ibuprofen) can be administered in an amount of about 5 mg to about 80 mg per day, for example, about 5 mg to about 60 mg per day, about 5 mg to about 50 mg per day, about 5 mg to about 40 mg per day, about 5 mg to about 30 mg per day, about 5 mg to about 20 mg per day, and/or about 5 mg to about 15 mg per day. The non-steroidal anti-inflammatory drug (e.g., ibuprofen) may be administered 1 to 4 times per day, such as 1 to 2 times per day. For example, ibuprofen may be administered in a once-daily dose of about 5 mg to 20 mg, preferably in a once-daily dose of about 10 mg.

Blister Packs and Kits

The invention further provides a group of individual delivery units, for example, a blister pack comprising blisters, containing a pharmaceutically acceptable salt or ester of cromolyn. Blister packs are known in the art, and generally comprise a solid support comprising a plurality of spaced bubbles or wells (collectively referred to herein as "blisters") for carrying a predetermined amount of medicament.

A film or membrane seals the wells, and is susceptible to puncture or release from the solid support to make the medicament available for delivery. The specific shape, proportions, and dimensions of the blister pack and the individual blisters can be adjusted for use in a particular delivery device. For example, the blister pack is optionally provided as a coil or a circular (e.g., carousel) cartridge for insertion in a dry powder inhaler, and the blisters are shaped as inverted cones or domes. Additionally, the number of blisters (corresponding to the number of doses) may be varied.

The blister pack is composed of a material that protects the contents of the blisters from exposure to the environment and is compatible for use with an inhalation device for delivering cromolyn to a patent. Suitable materials include, but are not limited to, PVC (polyvinyl chloride), PVC/PVDC (polyvinylidene chloride) blends, PE (polyethylene), PP (polypropylene), polystyrene, cellophane, polyester (e.g. a polyester terephthalate), paper, polyamide, PET (polyethylene terephthalate), COC (cyclic olefin copolymer), metallic (e.g., aluminum) foil and any blend thereof. Different materials may be layered to form individual blisters or the blister pack, if desired. Blister packs are further described in, for example, U.S. Pat. Nos. 5,497,763; 7,080,644; 7,828,150; 7,931,022; and 8,291,900, and International Patent Publication Nos. WO 1999/23180 and WO 1989/01348 (all of which are hereby incorporated by reference in their entirety, and particularly with respect to their respective descriptions of blister packs).

Generally, blisters have a maximum capacity of about 15 to 20 mg of ingredients, which includes both the active ingredient (i.e. cromolyn, or its pharmaceutically acceptable salt or ester) and pharmaceutically acceptable excipients.

In the context of the invention, the blisters of the blister pack contain about 3 mg to about 20 mg of a pharmaceutically acceptable salt or ester of cromolyn, for example, 3 mg to about 19 mg, 3 mg to about 18 mg, 3 mg to about 17 mg, about 3 mg to about 15 mg, about 3 mg to about 14 mg, about 3 mg to about 13 mg, about 3 mg to about 12 mg, about 3 mg to about 11 mg, about 3 mg to about 10 mg, about 3 mg to about 9 mg, about 3 mg to about 8 mg, about 3 mg to about 7 mg, about 4 mg to about 20 mg, about 6 mg to about 18 mg, about 8 mg to about 17.5 mg, or about 16.1 mg to about 19.9 mg of the pharmaceutically acceptable salt or ester of cromolyn. Optionally, additional amounts of pharmaceutically acceptable excipients are included in the blisters with the cromolyn. In some embodiments, a capsule is used instead of a blister. Capsules for inhaler devices are well known in the art.

The pharmaceutically acceptable salt or ester of cromolyn is provided in a solid dosage form, preferably a powder containing particles of the pharmaceutically acceptable salt or ester of cromolyn as described herein. The powder optionally comprises one or more pharmaceutically acceptable excipients, as described above. The pharmaceutically acceptable excipients, when present, are included in the powder in a total amount of about 0.1% to about 80% by weight, about 1% to about 80% by weight, about 5% to about 80% by weight, about 10% to about 80% by weight, about 15% to about 80% by weight, about 20% to about 80% by weight, about 25% to about 80% by weight, about 30% to about 80% by weight, about 35% to about 80% by weight, about 40% to about 80% by weight, about 20 to about 75% by weight, about 20% to about 70% by weight, about 20% to about 65% by weight, about 20% to about 60% by weight, about 25% to about 55% by weight, about 30% to about 50% by weight, about 35% to about 45% by weight, and/or about 40% by weight.

Alternatively, in some embodiments herein, the cromolyn is provided in liquid solution form.

In one example, the invention further provides a kit comprising a blister pack, such as the blister pack described herein, and a dry powder inhaler (DPI) device. In some embodiments, a kit comprises a capsule pack and a dry powder inhaler (DPI) device. In various embodiments, the device is an active dry powder inhaler device, such as a dry powder inhaler device that comprises a chamber comprising a piezoelectric vibrator for deaggregating a dry powder and an air flow passageway in which the deaggregated powder is picked up and carried for inhalation by a patient. The kit optionally includes one or more additional medicaments, such as a non-steroidal anti-inflammatory drug (e.g., ibuprofen, acetylsalicylic acid, diflunisal, salsalate, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, licofelone, hyperforin, and figwort). Such additional medicaments may be provided in any known dosage form, including solid dosage forms (e.g., tablets, capsules and powders) and liquid dosage forms (e.g., solutions, suspensions, emulsions, syrups and elixirs).

EXAMPLES

Example 1

A Next Generation Pharmaceutical Impactor (NGI) cascade impactor device (MSP Corporation, Shoreview, Minn., US) was used to assess delivery of cromolyn by four different inhaler devices.

Delivery of cromolyn by a single-use passive dry powder inhaler device was assessed. The passive inhaler device included an active particle dispersion mechanism (ACTIVEMESH, Aespira) involving breath-driven beating of a mesh package containing the powder to be delivered.

A blend containing disodium cromoglycate (DSCG) (Cambrex) and Lactohale LH300 lactose (Friesland Foods Domo) was prepared by blending in an Alpine Picoline high shear mixer (module Picomix) (Hosokawa Alpine, Augsburg, Germany) at a speed of 4000 rpm for 3 minutes. The blend contained 80:20 (wt./wt.) DSCG:lactose. Neat DSCG also was tested. The samples (neat cromolyn or cromolyn:lactose blend) were loaded into the passive dry powder inhaler device and tested using an NGI cascade impactor device at a flow rate of approximately 100 L/min for 2.4 seconds.

The results of testing are provided in Table 1. The passive inhaler device delivered only 3% of the initial dose of neat DSCG and only 6% of the initial dose of blended cromolyn to Stage 4 and higher of the NGI cascade impactor device.

TABLE 1

| DSCG:lactose [wt./wt.] | Initial DSCG dose [mg] | Fine Particle Dose <5 μm [μg] (% of initial dose) | Stages 4 to 8 [μg] (% of initial dose) | MMAD [μm] |
|---|---|---|---|---|
| 100:0 | 5 | 430 (9%) | 150 (3%) | >4 |
| 80:20 | 4 | 400 (10%) | 240 (6%) | >4 |

Delivery of cromolyn by a PROHALER pre-metered multidose passive dry powder inhaler device (Aptar) was assessed. The PROHALER inhaler was initially expected to more efficiently deliver cromolyn because the device creates rapidly fluctuating airflow/shear and turbulence to deagglomerate the particles emitted from the blister prior to oral inhalation by the patient. The PROHALER inhaler also included breath-triggered opening of a dose and a blister cartridge system.

Two blends containing disodium cromoglycate (DSCG) (Cambrex) and lactose monohydrate (DMV-Fonterra Excipients) (grade: lactohale 200 with 13% of fines) were prepared by blending at a speed of 90 rpm for 60 minutes. The blends differed in the relative amounts of DSCG and lactose, and contained either 50:50 (wt./wt.) DSCG:lactose or 20:80 (wt./wt.) DSCG:lactose. The blends were filled into blisterstrips, which were then assembled into a PROHALER inhaler device and tested using an NGI device at a flow rate of approximately 35 L/min.

The results of testing are provided in Table 2. The emitted dose represents the total quantity of DSCG fired into the impactor. The fine particle fraction is calculated as follows: fine particle fraction=100%*fine particle dose/emitted dose. A fine particle dose with particles less than 3 μm in size corresponds approximately to the amount of cromolyn delivered to Stage 4 and higher of the NGI device. Thus, the PROHALER inhaler device delivered only about 4.4% of the initial dose of blended cromolyn (50:50 blend) and only about 9.6% of the initial dose of blended cromolyn (20:80 blend) to Stage 4 and higher of the NGI cascade impactor device.

Delivery of cromolyn by an active dry powder inhaler device also was assessed. The inhaler device included injection molded plastic components, electronics, a battery, and drug filled blisters. The inhaler included a lever arm, upon actuation of which the blister was placed in contact with a piezoelectric vibrator within the device and then pierced by needles. The inhaler also included an airflow sensor which automatically turned on the piezoelectric vibrator after a minimum inspiratory flow rate was exceeded. Activation of the piezoelectric vibrator deaggregated the powder particles and aerosolized them out of the blister and into the inspiratory airstream. The inhaler included visual feedback at the start of dosing and as confirmation of successful completion of dosing, thereby facilitating improved patient compliance. Similar devices have been shown to deliver a consistent amount of a drug at each of the different flow rates tested, ranging from 20 L/min to 60 L/min.

A blend containing disodium cromoglycate (DSCG) (Cambrex) and lactose monohydrate (DFE Pharma) (grade: lactohale LH201) was prepared by blending at a speed of 150 rpm for 15 minutes. The blend contained 60:40 (wt./wt.) DSCG:lactose. Neat DSCG also was tested. The samples (neat cromolyn or cromolyn:lactose blend) were filled into blisters, which were then assembled into the inhaler device and tested using an NGI device at a flow rate of approximately 30 L/min for 2 seconds.

The results of testing are provided in Table 4. The fine particle dose is the amount of cromolyn recovered below a diameter of 5 μm. The fine particle fraction <5 μm is provided as a percentage of the amount of cromolyn recovered from the NGI cascade impactor device (i.e., the delivered dose). The active inhaler device delivered 42% of the initial dose of neat DSCG and 43% of the initial dose of blended cromolyn to Stage 4 and higher of the NGI cascade impactor device. Thus, in contrast to the results provided in Tables 1 to 3, the results for the active dry powder inhaler device demonstrate delivery of over 1.5 mg and over 30% of the administered dose to Stages 4 and higher of the NGI cascade impactor device.

TABLE 2

| DSCG:lactose [wt./wt.] | Initial DSCG dose [mg] | Emitted dose [mg] (% of initial dose) | Fine Particle Dose <3 μm [μg] (% of initial dose) | Fine Particle Fraction <3 μm [%] | MMAD [μm] |
|---|---|---|---|---|---|
| 50:50 | 3.9 | 2.4 (61%) | 170 (4.4%) | 8 | 3.9 |
| 20:80 | 1.6 | 1.1 (69%) | 154 (9.6%) | 15 | 3.1 |

In addition, delivery of cromolyn by a TWISTER inhaler device (Aptar) was assessed. The TWISTER inhaler device is a capsule-based dry powder inhaler. Compared to blisters, capsules typically have much higher drug loading capacities.

A blend containing disodium cromoglycate (DSCG) and lactose was prepared. The blend was assembled into a TWISTER inhaler device and tested using an NGI cascade impactor device at a flow rate of approximately 30 L/min.

The results of testing are provided in Table 3. The TWISTER inhaler device delivered only about 24% of the initial dose of blended cromolyn to Stage 4 and higher of the NGI cascade impactor device.

TABLE 3

| DSCG:lactose [wt./wt.] | Initial DSCG dose [mg] | Emitted dose [mg] (% of initial dose) | Fine Particle Dose <3 μm [μg] (% of initial dose) | Fine Particle Fraction <3 μm [%] | MMAD [μm] |
|---|---|---|---|---|---|
| 20:80 | 4.4 | 3.6 (82%) | 1065 (24%) | 29 | >4 |

TABLE 4

| DSCG:lactose blend | Initial DSCG dose [mg] | Fine Particle Dose <5 μm [μg] | Fine Particle Fraction <5 μm [% of delivered dose] | Stages 4 to 8 [μg] (% of initial dose) | MMAD [μg] |
|---|---|---|---|---|---|
| 100:0 | 5 | 2321 | 59 | 2098 (42%) | 2.6 |
| 60:40 | 5.8 | 2858 | 55 | 2505 (43%) | 2.8 |

Example 2

Pharmacokinetic Study of Cromolyn

Materials and Methods
Route of Administration.

An FDA-approved route of administration for cromolyn is oral inhalation using a capsule-based dry powder inhaler, with 20 mg cromolyn loaded per capsule. Studies have shown that with high inspiratory rates, the inhaled cromolyn is delivered to the human lung, with 10-15% of the inhaled drug-delivered dose absorbed into the bloodstream.

Cromolyn Preparation.

Cromolyn is supplied by Cambrex Proforma (Milan, Italy) and used to formulate a 17.1 mg dose of cromolyn for inhalation using inhalation grade excipients.

Cromolyn was micronized at Cambrex to achieve an average particle size of 5 microns or less. It is important for particles to be less than 10 microns, with the majority of particles falling between 2 and 5 microns, since this is necessary for successful deposition to the secondary bronchi of the respiratory tract following inhalation.

Cromolyn capsules for inhalation were manufactured by Pharmaterials, Ltd (Reading, UK). Initial characterization of the manufactured Cromolyn was performed by Pharmaterials and was found to be crystalline and hygroscopic material with particle size distribution suitable for inhalation (d50<5 μm and d90<10 μm). Therefore, there was a need to use hydrophobic excipient in the powder formulation to improve product performance and stability. Addition of hydrophobic excipient offers inherent resistance of dry powder inhalation formulations to negative effect of moisture to such formulations. Magnesium stearate was chosen as suitable hydrophobic excipient since it is commercially used in dry powder inhaler (DPI) products. Additionally, its safety profile is well studied and demonstrated for use in inhalation products. Lactose monohydrate was additionally used as diluent for this case. Each manufactured capsule of ALZT-OP1a contains 17.1 mg of cromolyn. The formulations (Cromolyn and Placebo) are shown in Table 5.

TABLE 5

ALZT-OP1a (Cromolyn) Formulation

| | | | ALZT-OP1a Composition | | | |
|---|---|---|---|---|---|---|
| | | | Placebo | | Drug Product | |
| Component | Quality Standard | Function | % w/w | mg/capsule | % w/w | mg/capsule |
| Cromolyn sodium (micronized) | USP | Active | — | — | 58.0 | 17.1[a] |
| Lactose monohydrate | NF | Diluent | 98.0 | 44.1 | 40.0 | 12.8 |
| Magnesium stearate (micronized) | NF | Stabilizer | 2.0 | 0.9 | 2.0 | 0.6 |
| Hydroxypropyl methylcellulose capsule[b] | In-house | Encapsulation | NA | NA | NA | NA |
| Total | | | 100% | 45 | 100% | 32 |

USP: United States Pharmacopeia;
NF: National Formulary
[a]Weight of cromolyn sodium, USP per capsules is 17.1 mg on an anhydrous basis (18.6 mg per capsule on as-is basis).
[b]Hydroxypropyl methylcellulose capsule functions only to meter and deliver the drug product through the dry powder inhaler and is not ingested during administration.

AZHALER.

The AZHALER DPI (239700001AB-Rs01) is a monodose inhaler device manufactured by Plastiape S.p.a (Italy) for use with ALZT-OP1a (cromolyn). It is a single-dose device used to deliver the inhalation powder to the patient's lung in form of an aerosol. The inhaler consists of a container, a valve, and a mouthpiece. In this study the low resistance model (80 L airflow resistance) was used. These device reaches a pressure drop of 4 kPa at c.80 L/min, and is suitable for use on a wide range of patient population i.e. including elderly, children and patients with severe respiratory impairment Dosage.

With AZHALER, the results show about 4-5 mg cromolyn (in the impactor fractions with <3 micron size particles needed for systemic uptake) per 17.1 mg of API (NGI stage 4-MOC see Table 1)

4-5 ee-3 g/512 g/mol=7.8-9.8 micromoles of cromolyn plasma levels

Assuming 0.2-1% uptake in brain from plasma=16-98 nanomoles divided by/1.5 L brain=11-66 nM cromolyn/L in brain (per day). Therefore, 17.1 mg cromolyn inhaled with AZHALER device is estimated to result in 11-66 nM concentrations in the brain.

Study Design.

The primary objective of the Phase I open-labeled study was to determine the PK of cromolyn in plasma and CSF, following administration of a single 17.1 mg inhaled dose of cromolyn. The study also evaluated the PK of cromolyn in plasma and CSF, following administration of 34.2 mg of cromolyn (administration of two consecutive inhaled doses of 17.1 mg taken not more than two minutes apart). The secondary objective of the study was to evaluate the safety and tolerability of a single or double dose of cromolyn following administration. The study population consisted of 24 normal, healthy volunteers between the ages of 55-75 in good general health, without respiratory disease, confirmed by pulmonary function testing.

Results

The results indicated that the PK profile of cromolyn in plasma was characterized by a rapid absorption phase, with an average $C_{max}$ of 46.7±33.0 ng/ml (range 14.0-133.0 ng/ml) at 22.8±16.6 min (range 6-60 min) after single dose (17.1 mg) inhalation and an average $C_{max}$ of 96.8±46.2 ng/ml (range 36.1-236.0 ng/ml) at 22.2±19.4 min (range 6-60 min) after double dose (34.2 mg) inhalation. The average apparent $t_{1/2}$ of cromolyn in plasma was 1.75±0.9 h (range 0.6-3.7 h) following single dose (17.1 mg) inhalation and 1.91±0.7 h (range 0.7-3.8 h) following double dose (34.2 mg) inhalation, indicating moderate clearance. The average $AUC_{0-inf}$ of cromolyn in plasma increased with the dose increase from 195.71±97.33 h*ng/ml (range 93.3-287.0 h*ng/ml) to 284.55±91.29 h*ng/ml (range 154.8-443.3 h*ng/ml) following single (17.1 mg) and double (34.2 mg) dose inhalation, respectively.

Cromolyn plasma PK parameters are summarized in Table 6.

TABLE 6

Plasma Pharmacokinetic Parameters for Cromolyn

| Dose | $AUC_{0-inf}$ (h * ng/ml) | $T_{0.5}$ (h) | $T_{max}$ (h) | $C_{max}$ (ug/L) | Cl/F (mL/h) | Vd/F (mL) |
|---|---|---|---|---|---|---|
| 17.1 mg | | | | | | |
| Mean (SD) | 195.71 (97.33) | 1.75 (0.847) | 0.38 (0.276) | 46.69 (32.965) | 108532.36 (65822.400) | 137487.60 (5916.345) |
| Median | 206.92 | 1.56 | 0.25 | 36.20 | 82640.18 | 134426.90 |
| Min, Max | 93.3, 287.0 | 0.6, 3.7 | 0.1, 1.0 | 14.0, 133.0 | 59593.2, 183363.7 | 133728.6, 144307.3 |
| 34.2 mg | | | | | | |
| Mean (SD) | 284.55 (91.29) | 1.91 (0.695) | 0.37 (0.323) | 96.75 (46.217) | 132178.06 (42254.442) | 330386.32 (133203.378) |
| Median | 262.31 | 1.80 | 0.23 | 76.50 | 130382.20 | 263533.00 |

Detectable levels of cromolyn in CSF were indicative of drug delivery to the brain. The average $C_{max}$ in CSF during the observed time interval of up to 4 hours was 0.24±0.077 ng/ml (range 0.2-0.4 ng/ml) at 3.72±0.704 h after single dose (17.1 mg) inhalation and 0.34±0.171 ng/ml (range 0.2-0.6 ng/ml) at 3.45±0.952 h after double dose (34.2 mg) inhalation. The observation period (0-4 hours) for the CSF samples was too short to allow for determination of $t_{1/2}$. The cromolyn AUC in plasma was 675 and 809 times higher than in CSF 2 hours after single (17.1 mg) and double (34.2 mg) dose inhalation and 232 and 299 times higher 4 hours after single and double dose inhalation, respectively.

These results indicate that inhaled cromolyn is transported via the deep lung to the blood, and then to the brain and CSF. The concentration of cromolyn in CSF increased up to the 4 hours of the lumber puncture.

Example 3

A Phase III Safety and Efficacy Study of ALZT-OP1 in Subjects with Evidence of Early Alzheimer's Disease Study Design.

Study Subjects.

This Phase III study is designed as a randomized, double-blinded, placebo-controlled study for subjects with evidence of early AD.

Subjects will be randomly assigned to the Group I arm which will consist of Cromolyn for inhalation, OR the Group II placebo arm, which will consist of inhaled placebo.

TABLE 7

Treatment Groups

| Group | Number of subjects | Treatment |
|---|---|---|
| I | 150 | ALZT-OP1a (q.d. inhalation of active cromolyn) |
| II | 150 | q.d. inhalation of placebo |

A minimum of 200 evaluable subjects will be randomized to receive one of two possible treatment assignments containing active study drug or placebo.

To account for subject dropouts (estimated rate of 30%), it is anticipated that up to 300 (or 150 subjects per treatment arm) may be recruited and randomized, to achieve a minimum of 100 evaluable subjects per treatment arm.

Dosage and Formulation.

Study drugs are dispensed as 12 or 24-week supplies at Day 1, Weeks 12, 24, and 48. Cromolyn powder blend or placebo will be filled into capsules for use with an AZHALER dry powder inhaler device. Each capsule will contain 17.1 mg of the active product ingredient (cromolyn) and inhalation grade lactose monohydrate as well as magnesium stearate as excipients, or placebo (lactose alone). The once-daily cromolyn dose to be tested in this study is about 21%, the dose from the four times daily approved dose level (80 mg cromolyn total per day [17.1/80]) for the treatment of asthma.

Study Regimen.

The total duration of subject participation is expected to be approximately 74 weeks or 7 visits. All subjects are required to have an initial screening visit (Day −21 to Day −1) to determine eligibility and a baseline visit (Day 1) to confirm eligibility prior to treatment start, and then asked to complete 72 weeks of daily dosing that requires them to return to the clinic at weeks 4, 12, 24, 48 and 72.

Study drug compliance and concomitant medication use will be evaluated at scheduled visits throughout the study.

Study Objective(s).

To evaluate the efficacy by CDR-SB assessment of a treatment regimen of oral inhaled cromolyn, compared to placebo.

To determine whether this treatment regimen slows down, arrests or reverses cognitive and functional decline in subjects with evidence of early AD.

Study Endpoints.

The primary endpoint of this study is a significant stabilization/improvement in cognitive and functional performance, as measured by the Clinical Dementia Rating test (CDR-SB), from baseline to Week 72, for subjects in the cromolyn treatment group compared to the placebo group.

Assessment of Efficacy

Methods for Assessing, Recording, and Analyzing Efficacy Parameters.

The primary efficacy variable will be analyzed using a mixed-effect model for repeated measures (MMRM) approach. The model will include the fixed effects treatment, visit, treatment by visit interaction, region (US, Europe, Asia/Pacific) and the covariates APOe4 (one or more alleles, no alleles), anti-dementia drug use (absent, present), baseline CDR-SB and age assuming an unstructured correlation matrix.

Clinical Dementia Rating (CDR).

The CDR is a clinical staging instrument for dementia. It characterizes six domains of cognitive and functional performance: Memory, Orientation, Judgment & Problem Solving, Community Affairs, Home & Hobbies, and Personal Care. The necessary information to make each rating is obtained through a semi-structured interview of the patient and a reliable informant or collateral source (e.g., a family member). The CDR questionnaire provides descriptive anchors that guide the clinician in making appropriate ratings based on interview data and clinical judgment. The CDR is conducted at Screening and at Weeks 12, 24, 48, and 72.

Global Clinical Dementia Rating (CDR): Disease Staging.

The Washington University Global CDR score (5 stages: 0, 0.5, 1, 2, 3) will be used as an inclusion criterion to screen and select a subject population consistent with early AD. Subjects are required to have a Global CDR score of 0.5 (mildly impaired), with the Memory Box score being at least 0.5. Each global score will be calculated using the Washington University online algorithm.

Clinical Dementia Rating-Sum of Bares (CDR-SB): Disease Severity.

The CDR-SB score (score range 0-18) will serve as the primary endpoint for the study and will be used for study group comparisons, monitoring disease progression, and evaluating treatment effect between active and placebo groups. A CDR-SB score of 0 represents normal functioning and a score of 18 represents severe impairment. Overall, the CDR-SB is expected to provide a more detailed quantitative general index than the Global CDR in patients with mild dementia. The CDR-SB is conducted at Screening and at Weeks 12, 24, 48, and 72.

Mini-Mental State Examination (MMSE).

The MMSE is a brief examination intended to evaluate an adult participant's level of cognitive functioning. The test is performed in following areas: orientation in time and place, learning and immediate recall, mental control and concentration, short-term recall, naming ability, language expression, verbal comprehension, writing comprehension, writing ability, and visual-spatial coordination. Scores range from 0 (maximum cognitive deficit) to 30 (no cognitive deficit). The MMSE is conducted at Screening and at Weeks 12, 24, 48, and 72.

Wechsler Memory Scale-Third Edition (WMS-III): Logical Memory II (LM II).

The Wechsler Memory Scale-Third Edition (WMS-III) is a neuropsychological test designed to measure different memory functions. The complete WMS-III is made up of eleven subtests:

1) Brief Cognitive Status Exam (Optional),
2) Visual Reproduction I,
3) Logical Memory I,
4) Spatial Addition,
5) Visual Reproduction II,
6) Logical Memory II,
7) Verbal Paired Associates I,
8) Designs I,
9) Symbol Span,
10) Verbal Paired Associates II,
11) Designs II.

In the current study, the Logical Memory II subtest will be used to assess delayed memory function. The WMS-III Logical Memory I (Immediate Recall) and Logical Memory II (Delayed Recall) will both be administered at Screening (only), but only the Logical Memory II score will be used as an inclusion criterion. LM II scores acceptable for inclusion will be categorized by subjects' years of education.

Logical Memory II will be administered 30 minutes after the administration of Logical Memory 1.

CF Biomarker Analysis.

CSF Aβ-42 levels ≥200 pg/mL and ≤600 pg/mL are required for study entry. Following consent for the CSF collection procedure, subjects who meet all other study entry requirements will undergo lumbar puncture for CSF collection at Screening (Day −21 to Day −1) to confirm study eligibility. On a voluntary basis, subjects may also provide CSF samples at End of Study (Week 72 or within 1 week following Week 72) for follow-up and change from baseline analyses. Duplicate CSF samples will be collected at Screening and End of Study. One Screening CSF sample will be analyzed to confirm study eligibility; the back-up sample will be stored frozen at −20° C. or −80° C. until study completion, at which point the sample will be shipped on dry ice to a central testing facility. End of Study samples will be stored frozen at −20° C. or −80° C. for subsequent analysis. Lumbar puncture should be performed according to clinical site protocols and follow current CSF sample standardization procedures.

The cromolyn monotherapy administered daily at the dose of 17.1 mg to patients having early stage AD can be as effective in stabilization/improvement of cognitive and functional performance as the combination therapy of cromolyn and ibuprofen.

What is claimed is:

1. A powder composition comprising about 16.1 mg to about 19.9 mg of a pharmaceutically acceptable salt or ester of cromolyn in the form of a powder comprising particles of the pharmaceutically acceptable salt or ester of cromolyn, the majority of particles having a diameter of about 2 to about 5 microns, wherein said composition is capable of being delivered using a device that deposits (a) at least 3.0 mg and (b) at least 20% by weight of the administered amount of pharmaceutically acceptable salt or ester of cromolyn to Stage 4 and higher of a Next Generation Pharmaceutical Impactor (NGI) cascade impactor device at a flow rate of 60-80 L/min.

2. The composition of claim 1, wherein the composition comprises about 17.1 mg of the pharmaceutically acceptable salt or ester of cromolyn.

3. The composition of claim 1, wherein the device is selected from the group consisting of a dry powder inhaler (DPI) device, a metered dose inhaler (MDI) device, and a dry powder nebulizer (DPN) device.

4. The composition of claim 1, wherein the device is a single-dose inhalation device that delivers the powder as an aerosol.

5. The composition of claim 1, wherein the composition further comprises one or more pharmaceutically acceptable excipients.

6. The composition of claim 1, wherein the composition comprises about 50% to about 60% (w/w) of the pharmaceutically acceptable salt or ester of cromolyn and about 40% to about 50% of one or more excipients.

7. The composition of claim 6, wherein the excipient is selected from the group consisting of a monosaccharide, a disaccharide, an oligosaccharide, a polysaccharide, a polyalcohol, and lactose.

8. The composition of claim 6, wherein the excipient is selected from the group consisting of lactose, mannitol, and sorbitol.

9. The composition of claim 1, wherein the composition does not comprise an active ingredient other than the pharmaceutically acceptable salt or ester of cromolyn.

10. The composition of claim 1, wherein the composition does not comprise a non-steroidal anti-inflammatory drug.

11. The composition of claim 1, wherein the composition does not comprise ibuprofen.

12. A method of delivering cromolyn to a patient in need thereof, comprising administering the powder composition of claim 1 to the patient via oral inhalation, wherein the particles of said powder have a mass median particle size (D50) of less than about 5 microns; and wherein the composition is administered using a device that deposits about 4 mg to about 5 mg of cromolyn to the secondary bronchi of the patient at a flow rate of 60-80 L/min.

13. The method of claim 12, wherein the method comprises administering about 17.1 mg of the pharmaceutically acceptable salt or ester of cromolyn, and wherein said composition optionally comprises one or more pharmaceutically acceptable excipients.

14. The method of claim 12, wherein the device is selected from the group consisting of a dry powder inhaler (DPI) device, a metered dose inhaler (MDI) device, and a dry powder nebulizer (DPN) device.

15. The method of claim 12, wherein administering comprises suspending the powder into an inhaled gas stream.

16. The method of claim 12, wherein administering comprises vibrating the powder at high frequency.

17. The method of claim 16, wherein the frequency is about 10 kHz to about 50 kHz.

18. The method of claim 14, wherein the device is a dry powder inhaler comprising a chamber comprising a piezoelectric vibrator or an ultrasonic vibrator for deaggregating a dry powder and an air flow passageway in which the deaggregated powder is picked up and carried for oral inhalation by a patient.

19. The method of claim 14, wherein the dry powder inhaler device is a single-dose device consisting of a container, a valve, and a mouthpiece.

20. The method of claim 14, wherein the device is a dry powder inhaler device.

21. The method of claim 12, wherein the powder comprises about 0.1% to about 80% by weight of an excipient.

22. The method of claim 12, wherein the powder comprises about 40% to about 80% by weight of an excipient.

23. The method of claim 12, wherein the powder comprises about 40% to about 45% by weight of an excipient.

24. The method of any one of claims 21-23 wherein the excipient is selected from the group consisting of a monosaccharide, a disaccharide, an oligosaccharide, a polysaccharide, and a polyalcohol.

25. The method of any one of claims 21-23 wherein the excipient is selected from the group consisting of lactose, mannitol, and sorbitol.

26. The method of claim 25, wherein excipient further comprises a hydrophobic salt.

27. The method of claim 26, wherein the hydrophobic salt comprises a stearate.

28. The method of claim 12, wherein said powder composition is administered at a frequency of one or two times daily.

* * * * *